US006306791B2

(12) United States Patent
Schaverien et al.

(10) Patent No.: US 6,306,791 B2
(45) Date of Patent: Oct. 23, 2001

(54) BRIDGED ZIRCONOCENE COMPOUNDS, PROCESS FOR THEIR PREPARATION AND THEIR USE AS CATALYST COMPONENTS IN THE POLYMERIZATION OF OLEFINS

(75) Inventors: Colin J. Schaverien, Amsterdam; René Ernst, Hoorn; Jan-Dirk van Loon, Almere, all of (NL); Tiziano Dall'Occo, Ferrara (IT)

(73) Assignee: Basell Technology Company BV, Hoofddorp (NL)

(*) Notice: Subject to any disclaimer, the term of this patent is extended or adjusted under 35 U.S.C. 154(b) by 0 days.

(21) Appl. No.: 09/795,894

(22) Filed: Feb. 28, 2001

Related U.S. Application Data

(62) Division of application No. 09/265,046, filed on Mar. 9, 1999, now Pat. No. 6,232,484.

(30) Foreign Application Priority Data

Mar. 9, 1998 (EP) .................................................. 98200728

(51) Int. Cl.[7] ............................. B01J 31/00; C07F 17/00; C07F 7/00
(52) U.S. Cl. .......................... 502/117; 502/103; 526/160; 526/943; 556/11; 556/12; 556/14; 556/20; 556/53; 556/54
(58) Field of Search ..................................... 502/103, 117; 526/160, 943; 556/11, 12, 14, 20, 53, 54

(56) References Cited

U.S. PATENT DOCUMENTS

| 5,646,322 | * | 7/1997 | Van Beek et al. | 556/11 |
| 5,948,873 | * | 9/1999 | Santi et al. | 526/129 |
| 5,990,253 | * | 11/1999 | Van Beek et al. | 526/127 |

FOREIGN PATENT DOCUMENTS

| 0 372 414 A2 | 6/1990 | (EP) . |
| 0 485 823 A1 | 5/1992 | (EP) . |
| WO 94/11406 | 5/1994 | (WO) . |

OTHER PUBLICATIONS

Cheng. "Comonomer sequence distribution in ethylene/ I–hexene copolymers." Polymer Bulletin, vol. 26, pp. 325–332 (1991).

Doi, et al. "Monomer Sequence Distribution in Ethylene–Propylene Copolymers Prepared with a Silica–Supported $MgCl_2/TiCl_4$ Catalyst." Makromol. Chem., Rapid Commun. vol. 4, pp. 169–174 (1983).

Hitchcock, et al. "Synthesis of ansa–Titanocenes from 1,2–Bis(2–indenyl)ethane and Structural Comparisons in the Catalytic Expoxidation of Unfunctionalized Alkenes." Onganonetallics 1995, vol. 14, pp. 3732–3740.

Nantz, et al. "A Disulfone–Based Approach to ansa–Titanocenes: Synthesis of (Ethylenebis (2–idenyl)) titanium Dichloride." Organometallics 1993, vol. 12, pp. 5012–5015.

Uozumi et al. "Copolymerization of olefins with Kaminsky–Sinn–type catalyts." Makromol. Chem. vol. 193, pp. 823–831 (1992).

\* cited by examiner

*Primary Examiner*—Porfirio Nazario-Gonzalez
(74) *Attorney, Agent, or Firm*—Bryan Cave LLP

(57) ABSTRACT

Zirconocene compounds with two indenyl ligands linked in the 2 position by means of a two-carbon-atoms divalent bridging group can be suitably used as components of catalysts for the polymerization of olefins. Particularly it is possible to prepare, with high yields, ethylene (co)polymers having low molecular weights and narrow molecular weight distributions, without the need of using considerable amounts of molecular weight regulators, such as hydrogen.

5 Claims, No Drawings

BRIDGED ZIRCONOCENE COMPOUNDS, PROCESS FOR THEIR PREPARATION AND THEIR USE AS CATALYST COMPONENTS IN THE POLYMERIZATION OF OLEFINS

This is a divisional of U.S. application Ser. No. 09/265,046, filed, Mar. 9, 1999, now U.S. Pat. No. 6,232,484.

FIELD OF THE INVENTION

The present invention relates to bridged zirconocene compounds, to the corresponding ligands, to a new process for their preparation and to the use of said zirconocenes as catalytic components in the polymerization of olefins.

PRIOR ART DISCLOSURE

Stereorigid chiral metallocene compounds possessing two bridged indenyl groups are well known in the state of the art and are mainly used as catalytic components in olefin polymerization processes, and in particular in the preparation of stereoregular polyolefins. The numbering of the substituents on the indenyl group, to which reference is made in the present application, in accordance with the IUPAC nomenclature, is the following:

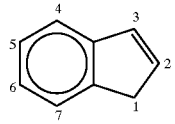

In the bridged indenyl metallocene compounds known in the state of the art, the indenyl groups are linked together by divalent radicals containing one or more carbon atoms and/or heteroatoms; the divalent bridging groups are generally linked to the 1 position of said indenyl groups, and therefore, the common indenyl metallocenes are 1-indenyl compounds. For example, the European patent application EP 0 485 823 describes a class of bridged bis(1-indenyl) metallocenes, wherein the indenyl groups have a substituent other than hydrogen in the 2 position and are bridged in the 1 position by means of a bridge containing 1 or more carbon atoms (e.g. an ethylene or isopropylidene group) or containing heteroatoms (e.g. a dimethyl-silyl or a diphenyl-silyl group).

The European patent application EP 0 372 414 describes a very broad class of bridged or unbridged metallocenes; among the many metallocenes exemplified, are reported two specific bis-indenyl metallocene compounds, wherein the divalent group bridging the indenyl groups is linked to the 1 position of one indenyl group and to the 2 position of the other indenyl group (formulae II-1 and II-2, on page 5 of said patent application).

The International patent application WO 94/11406 describes a very broad class of metallocene compounds of formula R'Ind-M-(Cp)$Q_k$, wherein: Ind is an indenyl group; R' is a substituent, other than hydrogen, linked in the 2 position of said indenyl group; Cp is a cyclopentadienyl group; M is a transition metal belonging to group 3, 4, 5 or 6 of the Periodic Table of Elements; and Q is a σ-ligand of the metal M, k being an integer linked to the valence of said metal M. Among the huge plethora of embodiments envisaged in the reported general formula, R' can form a bridge between the 2 position of the Ind group and the Cp group of the above formula; therefore, the class of bis(2-indenyl) compounds is generically described. The definition of the bridging group R' is very broad too, the preferred bridges linking the two indenyl residues being —S—, $(CH_3)_2Si<$ and —$CH_2$— groups; in fact, in the working examples only bis-indenyl zirconocenes with a one-atom-bridge have actually been synthesized and tested in ethylene (co) polymerization, giving ethylene homopolymers in very low yield and ethylene/propylene copolymers having very low molecular weights and in low yields too.

SUMMARY OF THE INVENTION

The Applicant has now unexpectedly found a new class of bridged bis(2-indenyl)zirconocenes, particularly active as catalyst components for the polymerization of olefins. Said zirconocene compounds are characterized by the presence of two indenyl ligands, bridged in the 2 position by means of a two-carbon-atoms divalent group. Therefore, an object of the present invention is a bridged zirconocene compound of formula (I):

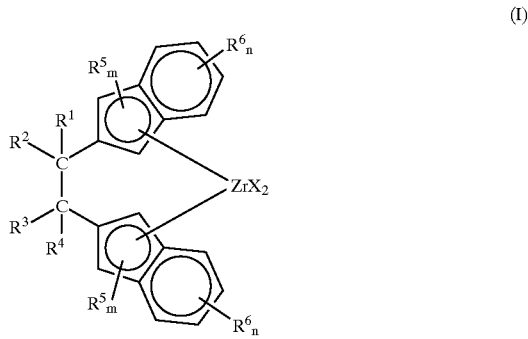

wherein $R^1$, $R^2$, $R^3$ and $R^4$, the same or different from each other, are selected from the group consisting of hydrogen, linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alylaryl and $C_7$–$C_{20}$ arylalkyl radicals, optionally containing one or more Si or Ge atoms, or wherein two substituents of $R^1$, $R^2$, $R^3$ and $R^4$ form a ring having from 4 to 8 carbon atoms;

$R^5$ and $R^6$, the same or different from each other, are selected from the group consisting of linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more Si or Ge atoms, or two vicinal $R^6$ substituents on the same indenyl group form a ring having from 4 to 8 carbon atoms;

m is an integer ranging from 0 to 2; n is an integer ranging from 0 to 4;

the groups X, the same or different from each other, are hydrogen, halogen, —R, —OR, —SR, —$NR_2$ or —$PR_2$, wherein R is selected from the group consisting of linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more Si or Ge atoms.

Another object of the present invention is a catalyst for the polymerization of olefins comprising the product obtainable by contacting:

(A) one or more bridged zirconocene compounds of formula (I), as described above, and (B) a suitable activating cocatalyst.

Furthermore, the present invention provides a process for the polymerization of olefins comprising the polymerization reaction of one or more olefinic monomers in the presence of a catalyst as described above.

Another object of the present invention is a ligand of formula (II):

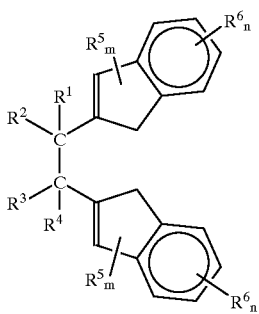

(II)

wherein $R^1$, $R^2$, $R^3$, $R^4$, $R^5$ and $R^6$, m and n have the meaning reported above, with the proviso that:

when $R^1$, $R^2$, $R^3$ and $R^4$ are hydrogen and n is 0, then m is different from 0; and when $R^1$, $R^2$, $R^3$ and $R^4$ are hydrogen, n is 0 and m is 1, then $R^5$ is different from $-CH_3$, $-CH_2Ph$ and $-Si(CH_3)_3$.

The present invention further concerns a process for the preparation of the above ligands of formula (II), comprising the following steps:

(1) reacting an adipic ester of formula (III) with at least 2 equivalents of a benzyl compound of formula (IV) and at least 2 equivalents of an alkali metal or alkaline earth metal base, in the presence of an organic solvent, to obtain an intermediate compound of formula (V); said step may be represented by the following reaction scheme:

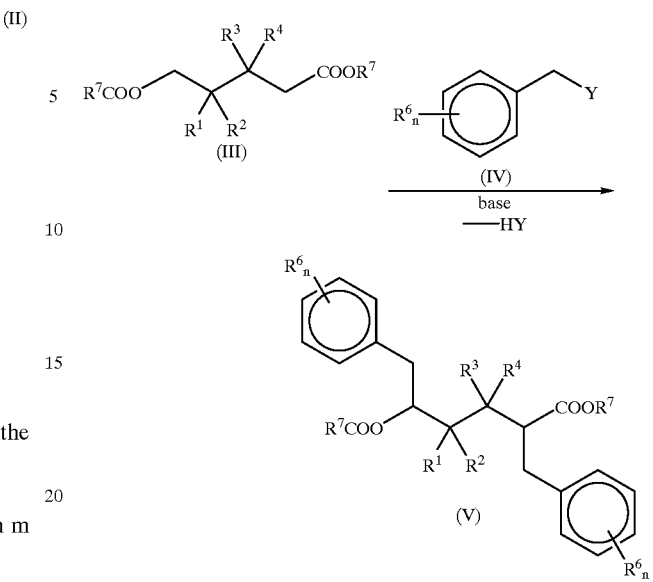

wherein $R^1$, $R^2$, $R^3$, $R^4$, $R^6$ and n have the meaning reported above, $R^7$ is selected from the group consisting of linear or branched, saturated or unsaturated $C_1$–$C_{20}$ alkyl $C_3$–$C_{20}$ cycloalkyl, $C_6$–$C_{20}$ aryl, $C_7$–$C_{20}$ alkylaryl and $C_7$–$C_{20}$ arylalyl radicals, and Y is a suitable leaving group;

(2) cycling said compound of formula (V) to obtain a compound of formula (VII); said step may be represented by the following reaction scheme:

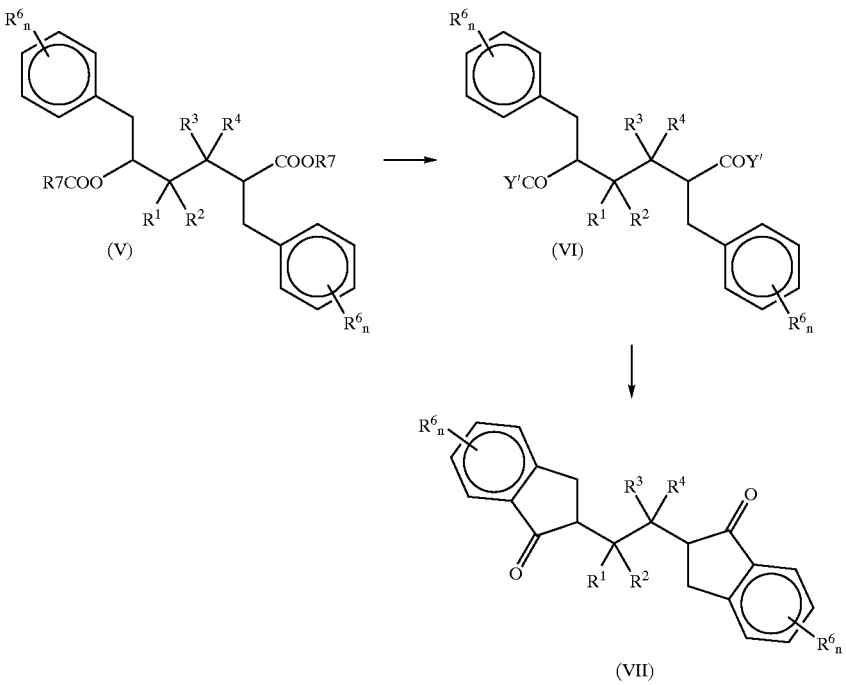

wherein $R^1$, $R^2$, $R^3$, $R^4$, $R^6$ and n have the meaning reported above and Y' is a suitable leaving group;

(3) reducing the ketonic functions of the indanyl moieties of the compound of formula (VII) to obtain the diol (VIII) and finally dehydrating the hydroxy functions of the indanyl moieties of said diol (VIII) to give the ligand (II); said step may be represented by the following reaction scheme:

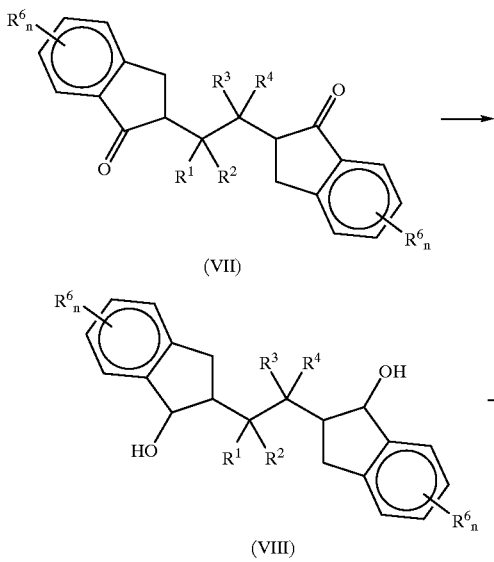

wherein $R^1$, $R^2$, $R^3$, $R^4$, $R^6$ and n have the meaning reported above.

When in the ligand of formula (II) m is ≠0, then the substituents $R^5$ can be introduced on the cyclopentadienyl ring by reacting a compound of formula (VII) or the same ligand of formula (II) with a suitable amount of an alkylating agent $R^5MgBr$, $R^5MgCl$ or $R^5_jB$, wherein B is an alkaline or alkaline-earth metal, and j is 1 or 2.

Finally, the present invention concerns intermediate compounds of formula (V), as reported above, useful in the synthesis of the ligands (II), according to the present invention.

DETAILED DESCRIPTION OF THE INVENTION

The bridged zirconocene compounds of formula (I), the corresponding ligands, the process for their preparation and the catalysts for the polymerization of olefins containing them, according to the present invention, will be better described in the following detailed description.

It is an object of the present invention a bridged zirconocene compound of formula (I), wherein $R^1$, $R^2$, $R^3$ and $R^4$, the same or different from each other, are selected from the group consisting of hydrogen, linear or branched, saturated or unsaturated, $C_1-C_{20}$ alkyl, $C_3-C_{20}$ cycloalkyl, $C_6-C_{20}$ aryl, $C_7-C_{20}$ alkylaryl and $C_7-C_{20}$ arylalkyl radicals, optionally containing one or more Si or Ge atoms, or wherein two substituents of $R^1$, $R^2$, $R^3$ and $R^4$ form a ring having from 4 to 8 carbon atoms. Preferably $R^1$, $R^2$, $R^3$ and $R^4$ are selected from the group consisting of hydrogen, methyl, ethyl, propyl, phenyl and benzyl; more preferably, $R^1$, $R^2$, $R^3$ and $R^4$ are hydrogen and the bridging group of the two 2-indenyl groups is ethylene.

In the bridged zirconocene compounds of formula (I), $R^5$ and $R^6$, the same or different from each other, are selected from the group consisting of linear or branched, saturated or unsaturated $C_1-C_{20}$ alkyl, $C_3-C_{20}$ cycloalkyl, $C_6-C_{20}$ aryl, $C_7-C_{20}$ alkylaryl and $C_7-C_{20}$ arylalkyl radicals, optionally containing one or more Si or Ge atoms; or two vicinal $R^6$ substituents on the same indenyl group form a ring having from 4 to 8 carbon atoms. $R^5$ and $R^6$ are preferably selected from the group consisting of methyl, ethyl, propyl, phenyl and benzyl.

The variable m is an integer ranging from 0 to 2; the variable n is an integer ranging from 0 to 4.

The groups X, the same or different from each other, are hydrogen, halogen, —R, —OR, —SR, —NR$_2$ or —PR$_2$, wherein R is selected from the group consisting of linear or branched, saturated or unsaturated, $C_1-C_{20}$ alkyl, $C_3-C_{20}$ cycloalkyl, $C_6-C_{20}$ aryl, $C_7-C_{20}$ alkylaryl and $C_7-C_{20}$ arylalkyl radicals, optionally containing one or more Si or Ge atoms. X is preferably Cl, Br or methyl.

Non-limiting examples of bridged zirconocene compounds according to the present invention are:

1,2-ethylene-bis(2-indenyl)zirconium dichloride and dimethyl, 1,2-ethylene-bis(1,3-dimethyl-2-indenyl)zirconium dichloride and dimethyl, rac- and meso-1,2-ethylene-bis(1-methyl-2-indenyl)zirconium dichloride and dimethyl, rac- and meso-1,2-ethylene-bis(1-ethyl-2-indenyl)zirconium dichloride and dimethyl, rac- and meso-1,2-ethylene-bis(4-phenyl-2-indenyl)zirconium dichloride and dimethyl, rac- and meso-1,2-ethylene-bis(1-methyl 4-phenyl-2-indenyl)zirconium dichloride and dimethyl, rac- and meso-1,2-ethylene-bis(1-isopropyl-4-phenyl-2-indenyl)zirconium dichloride and dimethyl.

Said bridged zirconocene compounds can be prepared by reaction of the corresponding ligands of formula (II) first with a compound capable of forming a delocalized anion on the cyclopentadienyl ring, and then with a compound of formula $ZrZ_4$, wherein the substituents Z, the same or different from each other, are halogen ($ZrCl_4$ is particularly preferred), according to common procedures known in the state of the art.

When, in the zirconocene of formula (I) one or more X groups are other than halogen, it is necessary to substitute one or more halogens Z of the zirconocene dihalide with one or more substituents X other than halogen. The substitution reaction can be carried out by standard procedures, known in the state of the art, for example by reacting the zirconocene dihalide with alkylmagnesium halides (Grignard reagents) or with alkyllithium compounds.

It is another object of the invention the ligand of formula (II), wherein $R^1$, $R^2$, $R^3$, $R^4$, $R^5$ and $R^6$, m and n have the meaning reported above, with the proviso that:

when $R^1$, $R^2$, $R^3$ and $R^4$ are hydrogen and n is 0, then m is different from 0; and when $R^1$, $R^2$, $R^3$ and $R^4$ are hydrogen, n is 0 and m is 1, then $R^5$ is different from —CH$_3$, —CH$_2$Ph and —Si(CH$_3$)$_3$.

In fact, ethylene-bridged bis-2-indenyl ligands, unsubstituted or bearing a substituent —CH$_3$, —CH$_2$Ph or —Si(CH$_3$)$_3$ have been disclosed by Nantz M. H. et al. in *Organometallics* 1993, 12:5012–5015 and by Hitchcock S. R. et al. in *Organometallics* 1995, 14:3732–3740. These ligands were used to prepare the corresponding titanocene dichloride, useful in the catalytic epoxidation of unfunctionalized alkenes. The ligands mentioned above are expressly excluded from the ligands according to the present invention.

The ligands of formula (II), according to the present invention, are prepared by means of a very simple and efficient process, which employs cheap starting materials and comprises single reaction steps having very high yields, some of them almost quantitative. Furthermore, said process does not require laborious and time-consuming purification procedures, being particularly suitable to large scale production.

The process step (1) comprises reacting the adipic ester of formula (III) with at least 2 equivalents, and preferably 2–4 equivalents of a benzyl compound of formula (IV) and at least 2 equivalents, and preferably 2–4 equivalents of an alkali metal or alkaline earth metal base, according to the reaction scheme reported in the summary of the invention, to obtain an intermediate compound of formula (V).

Said reaction is preferably carried out one pot, by sequential addition of said base and of the benzyl compound of formula (IV), in the presence of an organic solvent, at a temperature preferably ranging from 20 to 80° C., and more preferably from 50 to 70° C.

Said base of an alkali metal or alkaline earth metal is preferably selected from the group consisting of NaOEt, KOEt, KOH, NaOH, NaH, KH and mixtures thereof.

Said organic solvent is preferably selected from the group consisting of THF, glyme, toluene and mixtures thereof.

In said compound of formula (IV), Y is preferably Cl or Br.

Reaction step (2) comprises cycling the compound of formula (V), according to the reaction scheme reported in the summary of the invention, to obtain a compound of formula (VII). According to a preferred embodiment of the process of the invention, said step is conducted first de-esterifying the functions —COOR$^7$ of the compound of formula (V) to the corresponding —COOH groups, by adding at least 2 equivalents, and preferably 2–3 equivalents, of a base in a mixture of aqueous and organic solvent.

Said base is preferably KOH and/or NaOH. Said mixture of solvents is preferably a mixture of MeOH and water.

The present reaction step is preferably carried out at a temperature ranging from 20 to 150° C., and more preferably from 70 to 100° C., for a time of 1–5 hours, and more preferably for 2–3 hours.

The obtained diacid can be isolated by acidification, according to procedures known in the state of the art, and is subsequently derivatized with a suitable leaving group Y', to give a compound of formula (VI). Said group Y' is preferably Cl or Br.

When Y' is Cl, the compound of formula (VI) can be obtained from the above mentioned diacid by reaction with SOCl$_2$ in excess, and preferably in amounts ranging from 6 to 10 equivalents per leaving group Y', at a temperature preferably ranging from 20 to 80° C., and more preferably from 50 to 60° C., for a period preferably of 4–12 hours, and more preferably of 7–9 hours.

The compound of formula (VI) is then cycled to give the final compound (VII), in the presence of at least 1 equivalent of a Lewis acid, and preferably 1.1–1.3 equivalents of AlCl$_3$, at a temperature preferably ranging from 0 and 40° C., in the presence of an organic solvent. The compound (VII) can be finally isolated from the reaction mixture according to standard procedures.

Reaction step (3) comprises reducing the ketonic functions on the indanyl moieties of the compound of formula (VII) to obtain the diol (VIII) and finally dehydrating the hydroxy functions on the indanyl moieties of said diol (VIII) to give the ligand (II), according to the reaction scheme reported in the summary of the invention.

The compound (VII) can be reduced to the diol (VIII) by reaction with at least 0.5 equivalents, and preferably 1–1.2 equivalents, of a suitable reducing agent, in an organic solvent.

Said reducing agent is preferably selected from the group consisting of NaBH$_4$, LiAlH$_4$, NaH and KH; said organic solvent is preferably MeOlH. This reaction is preferably carried out at a temperature ranging from –20° C. to 20° C., for a time of 10–18 hours. The diol (VIII) can be then isolated by acidification, according to procedures known in the state of the art.

Said diol (VIII) is subsequently dehydrated to the ligand (II) by acid treatment or by thermolysis; in the former case, the diol (VIII) is preferably treated with catalytic amounts of an acid, more preferably p-toluensulfonic acid or HCl, in an organic solvent such as ether, toluene and CH$_2$Cl$_2$, at a temperature ranging from 20 to 100° C. In the latter case, the diol (VIII) is preferably dehydrated by thermolysis at a temperature ranging from 200 to 300° C., and more preferably from 250 to 270° C., for a period of 1–2 hours. The final ligand (II) can be then isolated according to standard procedures known in the state of the art.

When in the ligand of formula (II) m is ≠0, then the substituents R$^5$ can be introduced on the cyclopentadienyl ring by reacting a compound of formula (VII) or the same ligand of formula (II) with a suitable amount of an alkylating agent R$^5$MgX' or R$^5$$_j$B, wherein, X' is halogen, B is an alkaline or alkaline-earth metal and j is 1 or 2.

Preferably, the compound of formula (VII) or (II) is reacted with at least 2 equivalents of said alkylating agent, at a temperature ranging from –78° C. to 20° C., for a time of 1–3 hours. The reaction is preferably conducted in an organic solvent selected from the group consisting of THF, Ft$_2$O, toluene and mixtures thereof. Said alkylating agent is preferably selected from the group consisting of R$^5$MgBr, R$^5$MgCl, R$^5$Li, R$^5$$_2$Mg and R$^5$$_2$Zn.

The ligands of formula (II) according to the present invention can be easily transformed into the corresponding zirconocenes by using standard procedures known in the state of the art. Another object of the present invention are intermediate compounds of formula (V), useful in the synthesis of the ligards of formula (II):

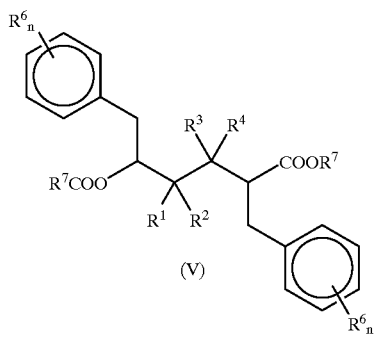

wherein R$^1$, R$^2$, R$^3$, R$^4$, R$^5$, R$^6$, R$^7$ and n have the meaning reported above.

The bridged zirconocene compounds according to the present invention can be advantageously used as catalytic components for the polymerization of olefins. Therefore, another object of the present invention is a catalyst for the polymerization of olefins, comprising the product obtainable by contacting the following components:

(A) one or more bridged zirconocene compounds of formula (I), as described above, and (B) a suitable activating cocatalyst.

Activating cocatalysts suitable as component (B) in the catalysts of the invention are linear, branched or cyclic alumnoxanes, containing at least one group of the type:

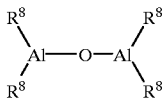

wherein the substituents $R^8$, the same or different from each other, are linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl radicals, or groups —O—Al($R^8$)$_2$.

Examples of alumoxanes suitable as activating cocatalysts in the catalysts according to the present invention are methylalumoxane (MAO), tetra-isobutyl-alumoxane (TIBAO), tetra-2,4,4-trimethylpentylalumoxane (TIOAO) and tetra-2-methyl-pentylalumoxane. Mixtures of different alumoxanes can also be used.

Activating cocatalysts suitable as component (B) in the catalysts of the invention are also the products of the reaction between water and organometallic aluminum compounds, preferably of formula $AlR^8_3$ or $Al_2R^8_6$, wherein $R^8$ has the meaning reported above.

Particularly suitable are the organometallic aluminum compounds of formula (II) described, in EP-A-575,875 and those of formula (II) described in WO 96102580. Non-limiting examples of organometallic aluminum compounds of formula $AlR^8_3$ or $Al_2R^8_6$ are: tris(methyl)aluminum, tris(isobutyl)aluminum, tris(isooctyl)aluminum bis(isobutyl)aluminum hydride, methyl-bis(isobutyl) aluminum, dimethyl(isobutyl)aluminum, tris(isohexyl) aluminum, tris(benzyl)aluminum, tris(tolyl)aluminum, tris (2,4,4-trimethylpentyl)aluminum, bis(2,4,4-trimethylpentyl) aluminum hydride, isobutyl-bis(2-phenyl-propyl)aluminum, diisobutyl-(2-phenyl-propyl)aluminum, isobutyl-bis(2,4,4-trimethyl-pentyl)aluminum and diisobutyl-(2,4,4-trimethyl-pentyl)aluminum.

Particularly preferred aluminum compounds are tris(2,4, 4-trimethylpentyl)aluminum (TIOA), and triisobutylaluminum (TIBA).

Mixtures of different organometallic aluminum compounds and/or alumoxanes can also be used.

The molar ratio between aluminum and the metal of the zirconocene is preferably comprised between about 10:1 and about 50,000:1, and preferably between about 100:1 and about 4,000:1.

Further activating cocatalysts suitable as component (B) in the catalysts of the invention are those compounds capable of forming an alkyl zirconocene cation. Non-limiting examples of these compounds are those of formula $Y^+Z^-$, wherein $Y^+$ is a Bronsted acid capable of donating a proton and of reacting irreversibly with a substituent X of the compound of formula (I), and $Z^-$ is a compatible anion which does not coordinate, which is capable of stabilizing the active catalytic species originating from the reaction of the two compounds, and which is sufficiently labile to be able to be displaced from an olefinic substrate. The $Z^-$ anion preferably comprises one or more boron atoms.

More preferably, the $Z^-$ anion is an anion of formula $BAr_4^{(-)}$, wherein the Ar substituents, the same or different from each other, are aryl radicals such as phenyl, pentafluorophenyl, bis(trifluoromethyl)phenyl. Tetrakis-pentafluorophenyl-borate is particularly preferred. Moreover, compounds of formula $BAr_3$ can be used conveniently.

The catalysts of the present invention can also be used on inert supports. This is achieved by depositing the zirconocene compound (A), or the product of its reaction with the activating cocatalyst (B), or component (B) and then the zirconocene compound (A), on inert supports such as silica, alumina or olefin polymers or prepolymer such as polyethylenes, polypropylenes or styrene-divinylbenzene copolymers. The thus obtained solid compounds, in combination with further addition of alkyl aluminum compound either untreated or pre-reacted with water, if necessary, is used advantageously in gas-phase polymerization.

The present invention also provides a process for the polymerization of olefins comprising the reaction of polymerization of one or more olefinic monomers in the presence of a catalyst as described above. Representative examples of olefinic monomers which may be used in the polymerization process of the invention are ethylene, α-olefins such as propylene and 1-butene, cycloolefins and conjugated diolefins.

The catalysts of the invention can be advantageously used in ethylene homopolymerization or in the copolymerization of ethylene with propylene, 1-butene, 1-hexene, 4-methyl-1-pentene or 1-octene. Said catalysts unexpectedly allow to obtain, in high yields, ethylene polymers having very low molecular weights and having narrow molecular weight distributions (MWDs), without the need of using substantial amounts of molecular weight regulators, such as hydrogen. In particular, with the catalysts of the invention it is possible to obtain, with high yields and without the use of molecular weight regulators, ethylene homopolymers or ethylene/α-olefin copolymers having intrinsic viscosities (I.V.) lower than 1.0 dl/g, preferably comprised between 0.2 and 0.8 dl/g, more preferably between 0.3 and 0.7 dl/g; furthermore, the obtained polymers have a molecular weight distribution MWD (Mw/Mn) lower than 3.

The catalysts of the invention not always show satisfactory activities in the homopolymerization of propylene to give atactic propylene oligomers. However, when the homopolymerization of propylene is performed in the presence of hydrogen, a very large increase in the activities is unexpectedly observed.

Therefore, according to another particular embodiment, the present invention provides a process for propylene homopolymerization, carried out in the presence of controlled amounts of hydrogen, which lead to a significant 100–500 fold increase in homopolymerization activity. The amount of hydrogen is preferably comprised between 1 mol % and 30 mol %, with respect to the total quantity of hydrogen and propylene, at the temperature of 50° C.; said amount of hydrogen is more preferably 2–3 mol % of a total amount of hydrogen and propylene.

The polymerization process according to the present invention can be carried out in the liquid phase, in the presence or absence of an inert hydrocarbon solvent, or in the gas phase. The hydrocarbon solvent can be either aromatic, such as toluene, or aliphatic, such as propane, hexane, heptane, isobutane and cyclohexane.

The polymerization temperature is generally comprised between −100° C. and +250° C., and more particularly between −50° C. and +100° C. The lower is the polymerization temperature, the higher are the molecular weights of the polymers obtained.

The molecular weight of the polymers can be further varied by changing the type or the concentration of the catalytic components or by using molecular weight regulators, for example hydrogen. Nevertheless, we stress again that the gist of the catalysts of the invention and of the polymerization process using them is the obtainment of polymers having a very low molecular weight, as well as a narrow MWD, which allow to avoid the presence of low soluble fractions in the final polymer.

The MWD can be varied by using mixtures of different zirconocene compounds, or by carrying out the polymerization in several steps that differ with respect to the temperatures of polymerization and/or the concentrations of molecular weight regulator.

The polymerization yields depend on the purity of the zirconocene component of the catalyst. Accordingly, the zirconocene compounds obtained by the process of the invention can be used as they are, or they can undergo purification treatments.

The components of the catalyst can be brought into contact with each other prior to polymerization. The duration of contact is generally between 1 and 60 minutes, preferably between 5 and 20 minutes. The pre-contact concentrations for the zirconocene component (A) are between $10^{-2}$ and $10^{-8}$ mol/l, whereas for component (B) they are between 10 and $10^{-3}$ mol/l. Precontact is generally effected in the presence of a hydrocarbon solvent and, if necessary, of small amounts of monomer.

The following experimental examples are given for illustrative and not limiting purposes.

GENERAL PROCEDURES AND CHARACTERIZATIONS

All the operations with the catalytic systems, the metallocenes and the aluminum alkyls were carried out under nitrogen atmosphere.

The zirconocenes and their intermediates were characterized by the following methods:

$^1$H-NMR and $^{13}$C NMR

The $^1$H-NMR and $^{13}$C-NMR spectra were recorded in $CD_2Cl_2$ (referenced against the middle peak of the triplet of residual $CHDCl_2$ at 5.35 ppm) and $C_6D_6$ (referenced against residual $C_6D_5H$ at 7.15 ppm), using a Varian Gemini 300 ($^1$H NMR at 300 MHz, $^{13}$C NMR at 75.4 MHz) or a Varian XL 200 ($^1$H NMR at 200 MHz, $^{13}$C NMR at 50.1 MHz). All NMR solvents were dried over 4 Å molecular sieves before use. Preparation of the samples was carried out under nitrogen, using standard inert atmosphere techniques; the measurements were performed at 20° C.

All the polymerization solvents were used after drying over molecular sieves and deoxygenated; ethylene was used as polymerization grade reagent; 1-hexene was dried over alumina and distilled over $LiAlH_4$. The polymers were characterized by the following methods:

VISCOSITY

Intrinsic viscosities I.V. were measured at 135° C. in tetrahydronaphtalene (THN) or in decalin.

THERMAL ANALYSIS

Calorimetric measurements were performed by using a differential scanning calorimeter Perkin Elmer DSC-7. The instrument was calibrated with indium and tin standards. Weighted sample (5–10 mg) was sealed into aluminum pans, heated to 200° C. and kept at that temperature for a time enough (5 minutes) to allow a complete melting of all the crystallites. Successively, after slow cooling at 20° C./min to 0° C., the peak temperature was assumed as crystallization temperature (Tc). After standing 5 minutes at 0° C., the sample was heated to 200° C. at a rate of 10° C./min. In this second eating run, the peak temperature was assumed as melting temperature (Tm) and the area as global melting enthalpy ($\Delta H_f$).

SIZE EXCLUSION CHROMATOGRAPHY (SEC)

Molecular weights (Mw) and molecular weight distributions (Mw/Mn) were determined by SEC analysis performed by using a "WATERS 200" GPC instrument, working at 135° C. in 1,2-dichlorobenzene stabilized with BHT (2,6-di-t-butyl-4-methyl-phenol) 0.1 wt %.

$^{13}$C-NMR.

The amounts of 1-hexene (C6) units in the ethylene/1-hexene copolymers were determined at 120° C. by a Brucker AC-200 spectrometer operating at 200.13 MHz in the Fourier Transform mode. The powder polymer samples were dissolved in 1,1,2,2-tetrachloro-1,2-dideuteroethane ($C_2D_2Cl_4$) to give an 8% w/v. concentration. Peak assignments and composition calculations were made according to the method described by H. C. Cheng et al. in *Polymer. Bull.* (vol.26, page 325, 1991). The triad and dyads distributions, as well as the kinetic parameters $r_1$ and $r_2$ were calculated by $^{13}$C-NMR analysis, according to the method described by T. Uozumi and K. Soga (*Macromol. Chem.*, 193:823, 1992).

The characterization of the propylene polymers and the determination of the amount of propylene (C3) units in ethylene/propylene copolymers were carried out on a Brucker 500 spectrometer, operating at 125.4 MHz. The samples were dissolved in 1,2,4-trichlorobenzene with some 1,4-dichloro-deuterohexene (1,4-$C_6D_4Cl_2$) added as lock. The measurements were done in 5 mm NMR tubes at 130° C., with a 70° pulse and a relaxation delay of 15 seconds. The characterization of ethylene/propylene copolymers was made according to the method described by Y. Doi et al. in *Makromol. Chem. Rapid Comm.* (vol.4, page 169, 1983).

CATALYST COMPONENTS

Methylalumoxane (MAO)

A commercial (Witco, MW 1400) 10% w/w toluene solution of MAO was dried in vacuum, at 60° C., to obtain a white free-flowing powder. Said powder was solubilized in toluene (1M solution) before use.

Tris(2,4,4-trimethyl-pentyl)aluminum (TIOA)

The product commercially available from WITCO was used diluted to a 1 M solution in heptane.

Tris(2-methyl-propyl)aluminium (TIBAL)

The commercial product was purchased from Witco and used as a 1M solution in hexane.

ZIRCONOCENE SYNTHESIS

SYNTHESIS 1
1,2-ETHYLENE-BIS(2-INDENYL)ZIRCONIUM DICHLORIDE (a) Preparation of the ligand 1,2-bis(2-indenyl)ethane Preparation of the diethyl ester of 2,5-dibenzyl-adipic acid from diethyl adipate

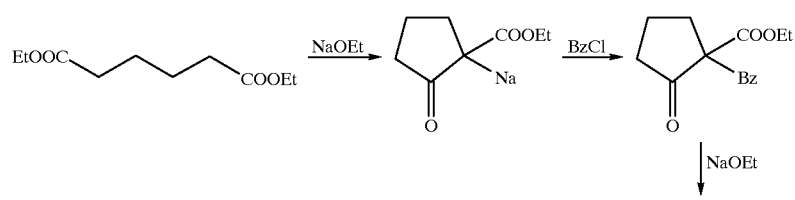

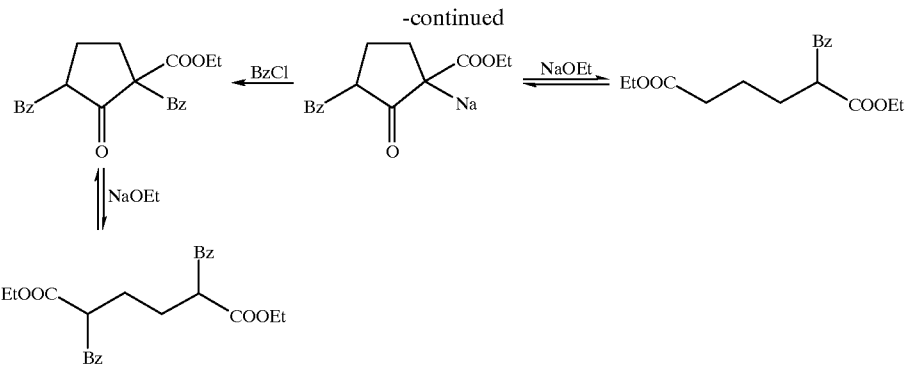

487 g of NaOEt (6.87 mol, 1.2 equivalents) were suspended in 3.54 kg of THF, in a 10 L cylindrical double-walled glass reactor, equipped with overhead stirrer and oil heating/cooling bath. The obtained suspension was heated to 60° C. and 1170 g (5.73 mol) of diethyl adipate were added, over a period of 1 hour.

The reaction mixture was stirred for 16 hours, at 60° C., and 820 g (6.41 moles, 1.12 equivalents) of benzyl chloride were added, over a period of 3.75 hours. The resulting product, the diethyl ester of 2-benzyl adipic acid, was maintained under stirring for other 3.5 hours, at 60° C., and the mixture was then allowed to cool to room temperature. 487 g (6.87 moles, 1.2 equivalents) of NaOEt were added to the mixture, over a period of 2 hours, at 23° C., and the reaction was then slowly warmed to 60° C., for 4 hours, and finally stirred for 16 hours at 60° C.

To the thus obtained mixture were then added 879 g (6.87 moles, 1.2 equivalents) of benzyl chloride, over a period of 1.75 hours. The reaction mixture was stirred at 65° C. for 6 hours and then cooled to 30° C.; an additional 100 g (1.47 moles) of NaOEt were added and, after 5 hours at 60° C., further 207 g (1.62 moles) of benzyl chloride were added, over a period of 1.75 hours, in order to convert the unreacted NaOEt into PhCH$_2$OEt. After 2 hours at 60° C., to the obtained mixture were added 224 g (4.87 moles, 0.85 equivalents) of EtOH and the reaction mixture was allowed to cool to 25° C. After the addition of 2,800 ml dilute HCl (pH 2), 1.43 kg toluene were added and the organic and aqueous layers were separated. The solvents were removed on a rotary evaporator and the higher boiling fractions (namely the excess of benzyl chloride and benzyl ether) were removed on a Schlenk line, at 100° C.

This purification procedure gave 2,035 g of dibenzyl adipate, having a purity of 95% (92% yield).

$^1$H NMR (CDCl$_3$): δ 7.37–7.1 (m, 10H), 4.04 (q, 4H, CH$_2$), 2.9 (m, 2H), 2.7 (m, 2H), 2.6 (m, 2H), 1.65 (m, 2H), 1.55 (m, 2H), 1.13 (t, 3H, Me), 1.125 (t, 3H, Me). $^{13}$C NMR (CDCl$_3$): δ 174.8 and 176.26 (COOH, diastereomers), 138.86 (C), 128.6 (CH), 128.06 (CH), 126.06 (CH), 59.91 (CH$_2$), 47.17 and 46.88 (CH, diastereomers), 38.18 and 38.03 (CH$_2$, diastereomers), 29.28 and 29.18 (CH$_2$, diastereomers), 13.90 (Me).

De-esterification of the diethyl ester of 2,5-dibenzyl-adipic acid

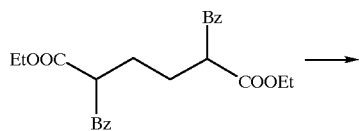

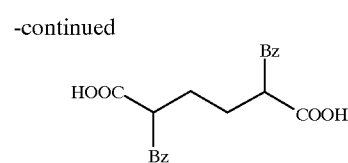

In a 3 L 3-neck round bottom flask, equipped with an overhead stirrer, were added 723 g (1.89 moles) of diethyl ester of 2,5-dibenzyl-adipic acid, obtained as described above, and 910 ml (5.67 moles) of Claisen alkali solution (a 6.25M solution of KOH in a 1:3/H2O:MeOH (v/v) mixture) and the obtained mixture was heated to 90° C. After 3 hours, the reaction mixture was cooled and transferred to a 2 L flask, and the MeOH was removed on a rotary evaporator. The mixture was then washed with 800 mL ether, in order to remove organic impurities, and the obtained viscous water solution was poured into a 5 L beaker, diluted with 1 L water and cooled using an ice bath, to a temperature of about 10° C. To the solution, maintained under constant stirring, was slowly added concentrated HCl, always maintaining the temperature at about 10–15° C.

At a pH value of about 3, a copious white/beige powdery precipitate formed; concentrated HCl was added until a pH of 1 to 2 was reached, obtaining a final solution of about 4 L. The white precipitate was isolated by filtration and washed with 300 ml water, thus obtaining 2,5-dibenzyl-adipic acid, as a white powder. After drying in a vacuum oven (at 200 mmHg, under nitrogen stream, at 70° C. to remove residual water) to constant weight, 598 g of pure 2,5-dibenzyl-adipic acid were isolated (yield 97% wt.).

$^1$H NMR (CD$_3$OD, 300 MHz): δ 7.10 (m, 10H, aromatic), 2.90 (m, 2H), 2.70 (m, 4H), 1.60 (m, 4H) ppm. $^1$H NMR (d$^8$-THF): δ 10.7 (br s, 2H, OH), 7.21–7.08 (m, 10H), 2.9 (dd, 2H), 2.62 (dd, 2H), 2.56 (m, 2H), 1.70 (m, 2H), 1.52 (m, 2H). $^{13}$C NMR (d$^8$-THF): δ 176.3 and 176.26 (COOH, diastereomers), 140.84 (C), 129.75 (CH), 128.88 (CH), 126.74 (CH), 47.94 and 47.82 (CH, diastereomers), 39.00 and 38.9 (CH$_2$, diastereomers), 30.33 and 30.36 (CH$_2$, diastereomers).

Preparation of 2,5-dibenzyl-adipic acid dichloride

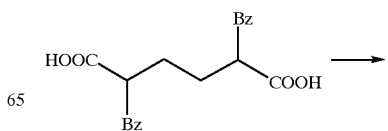

-continued

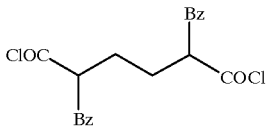

In a 2 L pear-shaped flask, were added 598 g (1.833 moles) of the 2,5-dibenzyl-adipic acid, prepared as described above, and 2,050 ml of SOCl₂ (17.22 mol, density=1.63 g/mL). The obtained mixture was stirred for 16 hours at 20° C., and then heated at 55° C. for 7 hours, thus giving a homogeneous solution; a rapid but controlled gas evolution was observed. After removal of SOCl₂ in excess, under vacuum at a bath temperature of 60° C., 300 mL toluene were first added and subsequently removed under vacuum, at 50° C., in order to remove any residual SOCl₂. A viscous light brown oil was isolated, which proved to be 2,5-dibenzyl-adipic acid dichloride (two diastereisomers were obtained).

$^1$H NMR (CDCl₃, 300 MHz): δ 7.4–7.2 (m, 8H, aromatic H), 3.14 (m, 4H), 2.87 (m, 2H), 1.80 (m, 4H) ppm. $^{13}$C NMR (CDCl₃, 75 MHz): δ 28.23 (CH₂), 28.33 (CH₂), 37.48 (CH₂), 37.70 (CH₂), 58.43 (CH), 58.54 (CH), 127.3 (CH, aromatic), 128.95 (CH, aromatic), 129.06 (CH, aromatic.), 137.1 (C), 176.15 (C=O) ppm.

Conversion of 2,5-dibenzyl-adipic acid dichloride to the corresponding bis(indanone)

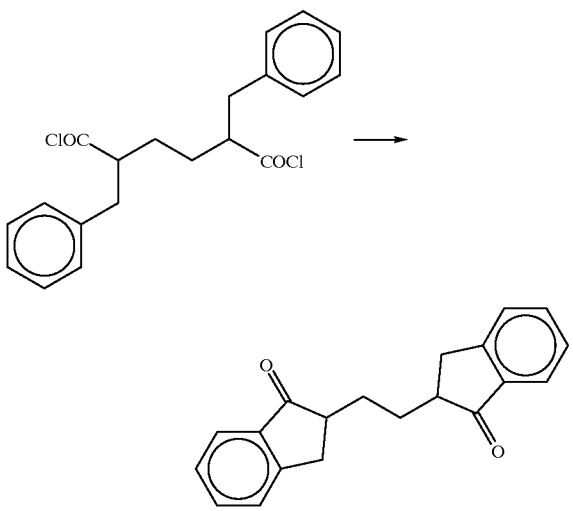

In a 3 L 3-neck flask, equipped with a large dropping funnel and kept under nitrogen, 605 g (4.53 moles; 24% excess) of AlCl₃ (99%, from Aldrich) were suspended in 800 mL of CH₂Cl₂, previously dried over molecular sieves; to the obtained suspension was slowly added, over a period of 3 hours, the 2,5-dibenzyl-adipic acid dichloride, prepared as described above, previously dissolved in 1200 ml of CH₂Cl₂. After stirring for 16 hours at 20° C., venting away the formed HCl, an orange suspension was obtained. This was carefully poured into a water/ice mixture, in a 5 L beaker, and the yellow CH₂Cl₂ layer was separated; the aqueous phase was extracted with 4×250 ml of CH₂Cl₂. The CH₂Cl₂ fractions were collected together and dried with anhydrous MgSO₄, thus obtaining a clear red-orange solution. Said solution was filtered and the solvent removed in vacuum, to afford a slightly sticky white solid. After washing with 500 ml pentane, 598 g of the bis(indanone) were isolated in the form of a white powder (yield of 93% wt. from 2,5-dibenzyl-adipic acid).

$^1$H NMR (CDCl₃, 300 MHz): δ 7.7–7.3 (m, 8H, aromatic H), 3.3 (dd, 2H), 2.85 (m, 2H), 2.63 (m, 2H), 2.1 (m, 2H), 1.60 (m, 2H) ppm. $^{13}$C NMR (CDCl₃, 75 MHz): δ 28.6 (CH₂), 29.3 (CH₂), 32.47 (CH₂), 32.69 (CH₂), 46.94 (CH), 47.47 (CH), 123.9, 126.65 (CH, aromatic), 127.44 (CH), 134.85, 136.71, 153.78, 208.6 (C=O) ppm.

Conversion of the above bis(indanone) to the corresponding diol

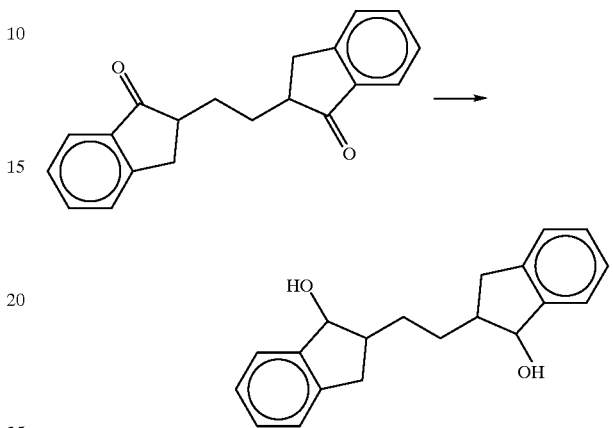

In a 5 L beaker, 494 g (1.70 moles) of the bis(indanone) prepared as described above were suspended in 3 L of THF and 1 L MeOH. After cooling the obtained mixture to about 10° C., with an ice bath, 71 g (1.87 moles) of NaBH₄ were slowly added, over a period of 3 hours, maintaining the suspension under vigorous stirring. The addition of NaBH₄ resulted in immediate gas evolution. The reaction mixture was maintained under stirring for 16 hours, at 20° C., and then THF and MeOH were removed on a rotary evaporator, thus giving a thick beige slurry. 2 L of water were added to said slurry and the obtained mixture was acidified with dilute HCl till a pH value of 3; a beige powder precipitated and was isolated by filtration. Said powder was extensively washed with water and finally dried to constant weight in a vacuum oven, at 75° C., finally obtaining 506 g of diol.

$^1$H NMR (CDCl₃, 300 MHz): δ 7.05–7.4 (m, 10H, aromatic), 5.13 (d, J=6), 5.05 (dd, J=6), 4.87 (d, J=6) total 2H, 3.1 (m), 2.9 (m), 2.75(m), 2.5(m), 2.4–2.1 (m), 2.0–1.6 (m) ppm.

Dehydration of the diol to give 1,2-bis(2-indenyl)ethane 300g of the diol, prepared as described above, were placed in a 1 L 3 neck round-bottom flask, in a heating mantel; this was heated to a temperature of about 260° C., under nitrogen stream to remove water. The diol melted at about 190° C. The thermolysis was stopped after about 2 hours, thus obtaining a product in the form of a "melted glass"; to this product were added 500 ml of CH₂Cl₂, by stirring and scratching in order to solubilize said melted glass. The resulting mixture was filtered through a frit, thus isolating the insoluble product, that resulted to be 1,2-bis (2-indenyl)ethane. After washing with pentane, 33.7 g of 1,2-bis(2-indenyl)ethane with a purity of 98.95% (GLC analysis) were isolated, in the form of a white powder.

CH₂Cl₂ was removed under vacuum from the CH₂Cl₂-soluble fraction, to give a slightly oily orange powder. Said powder was washed with pentane to give 74.4 g of 1,2-bis (2-indenyl)ethane in the form of a 96% pure light beige powder.

Totally were isolated 108.1 g of the desired ligand 1,2-bis(2-indenyl)ethane, with a 42% yield.

$^1$H NMR (CDCl₃): δ 7.5–7.1 (m, 4H), 6.63 (s, 1H), 3.39 (s, 2H, CH), 2.86 (s, 2H, CH₂). $^{13}$C NMR (CDCl₃): δ 150.1, 145.9, 143.4, 127.1, 126.7, 124.2, 123.8, 120.5, 41.5 (CH₂), 31.0 (CH₂).

(b) Preparation of the zirconocene dichloride

In a 2 L 3-necks round bottom flask, under nitrogen stream, to 146 g (0.566 moles) of 1,2-bis(2-indenyl)ethane was added 1 L Et$_2$O and the obtained mixture was cooled to −5° C. by means of a ice/salt bath. To this mixture were slowly added 475 ml of a 2.5 M n-BuLi solution in hexane (2.1 equivalents), over a period of about 2.5 hours. A beige slurry of the dianion was obtained. After having completed the addition, the mixture was stirred for a further 30 minutes, without ice bath, leading to a temperature of 14° C.

The volume of the obtained solution was reduced to about 1 L, by removing the solvent under vacuum. This solution was then cooled to −78° C. and added to a suspension of 132 g (0.566 moles) of ZrCl$_4$ in 500 ml of CH$_2$Cl$_2$, in a 2L 3-necks round bottom flask, previously cooled to −78° C. A bright yellow suspension was rapidly obtained. Said suspension was allowed to warm slowly to 20° C. and was stirred for further 16 hours, at 20° C. The solvent was then removed under vacuum, to give a light yellow powder. The pure final product was separated from LiCl and from polymeric byproducts by Soxhlet extraction with CH$_2$Cl$_2$, thus obtaining 197 g of 1,2-ethylene-bis(2-indenyl)zirconium dichloride (yield of 83% wt.).

$^1$H NMR (C$_6$D$_6$): δ 7.5 (dd, 4H), 6.95 (dd, 4H), 5.85 (s, 4H), 2.52 (s, 4H). $^1$H NMR (CD$_2$Cl$_2$): δ 7.5 (dd, 4H), 7.15 (dd, 4H), 6.42 (s, 4H), 3.33 (s, 4H). $^{13}$C NMR (CD$_2$Cl$_2$): δ 140.6 (2C), 129.4 (4C), 126.1 (4CH), 125.5 (4CH), 103.1 (4CH), 31.1 (2CH$_2$). Elemental analysis: Calculated: C 57.40; H 3.85. Found: C 57.29; H 4.00.

SYNTHESIS 2
1,2-ETHYLENE-BIS(2-INDENYL)ZIRCONIUM DIMETHYL 150 mg of 1,2-ethylene-bis(2-indenyl)zirconium dichloride, obtained as described in Synthesis 1, were suspended in 10 ml toluene and cooled to −78° C. 2 equivalents of MeLi we re added and the reaction mixture was allowed to warm to room temperature. The reaction mixture was centrifuged and toluene was removed in vacuum, thus obtaining 80 mg of 1,2-ethylene-bis(2-indenyl)zirconium dimethyl.

$^1$H NMR (C$_6$D$_6$): δ 7.33 (m, 4H), 6.8 (m, 4H), 5.73 (s, 4H, =CH), 2.29 (m, 4H, CH$_2$ bridge), −1.02 (s, 6H, Zr-Me).

SYNTHESIS 3
Rac- AND meso-1,2-ETHYLENE-BIS(1-METHYL-2-INDENYL) ZIRCONIUM DICHLORIDE (a) Preparation of the ligand 1,2-bis(1-methyl-2-indenyl) ethane 1.5 g (5.8 mmol) of 1,2-bis(2-indenyl)ethane, prepared as described in the above reported Synthesis 1(a), was dissolved in 25 ml THF and cooled to 0° C. n-BuLi (7.4 ml of a 1.6 M solution in hexane) was added and the resulting orange/brown solution stirred for 1 hour. This was added via a cannula to a solution of MeI (0.9 ml, 14.5 mmol) dissolved in 10 ml THF, at 0° C. After 2 hours, the THF was removed under vacuum and Et$_2$O was added. This Et$_2$O solution was washed 3 times with a saturated solution of NaHCO$_3$ and 3 times with a saturated aqueous solution of NaCl. After drying over MgSO$_4$, 1.4 g of yellow crystalline 1,2-ethylene-bis(1-methyl-2-indenyletaane was obtained. The ratio of double bond isomers is ca. 10:1. NMR data are reported for the major double bond isomer, i.e. the rac-isomer.

$^1$H NMR (CDCl$_3$): δ 7.45–7.10 (m, 8H), 6.53 (s, 2H), 3.43–3.30 (m, 2H, CHMe), 2.90–2.60 (m. 4H, CH$_2$-bridge), 1.36 (d, 6H, 7.5 Hz, Me). $^{13}$C NMR (CDCl$_3$): δ 154.7 (C), 148.8 (C), 144.0 (C), 126.5 (CH), 124.8 (CH), 123.9 (CH), 122.5 (CH), 120.0 (=CH), 46.2 and 46.0 (asynnmetric CHMe), 28.1 (CH$_2$-bridge), 15.8 (Me).

(b) Preparation of the zirconocene 4.1 ml of a solution 2.5 M of nBuLi in hexane were added to 1.4 g 1,2-ethylene-bis(1-methyl-2-indenyl)thane, prepared as described above, in 50 ml Et$_2$O cooled to 0° C. After 45 minutes, Et$_2$O was removed in vacuum and the resulting dianion was suspended in 80 ml toluene, at 20° C., in a drybox. 1.15 g (4.93 mmol) of ZrCl$_4$, in the form of a slurry in 10 ml toluene, were added and the reaction mixture changed from yellow to dark brown. After stirring for 21 hours at 20° C., the toluene solution was separated by centrifugation and the remaining solid was extracted with 3×25 ml toluene. The toluene extracts were combined, concentrated and crystallized at −35° C., thus giving 300 mg of rac-1,2-ethylene-bis(1-methyl-2-indenyl)zirconium dichloride. The toluene-insoluble precipitate obtained from the reaction mixture was extracted with CH$_2$Cl$_2$; CH$_2$Cl$_2$ was removed in vacuum, thus giving a yellow powder. This was washed with 2×5 ml pentane to afford 230 mg of pure meso-1,2-ethylene-bis(1-methyl-2-indenyl)zirconium dichloride.

Rac-isomer:

$^1$H NMR (C$_6$D$_6$): δ 7.54–7.34 (m, 4H), 7.21–7.10 (m, 4H), 6.16 (s, 2H, =CH), 3.63–3.45 (m, 2H, CH$_2$ bridge), 3.20–3.03 (m, 2H, CH$_2$ bridge), 2.48 (s, 6H, Me). $^{13}$C NMR (CD$_2$Cl$_2$): δ 137.7 (C), 129.8 (C), 128.9 (C), 126.2 (CH), 125.6 (CH), 125.4 (CH), 123.5 (CH), 116.3 (C-Me), 97.9 (CH), 27.6 (CH$_2$-bridge), 11.81 (Me). Elemental analysis: Calculated: C 59.18; H 4.51. Found: C 58.94; H 4.57.

Meso-isomer:

$^1$H NMR (C$_6$D$_6$): δ 7.54–7.46 (m, 2H), 7.41–7.33 (m, 2H), 7.24–7.06 (m, 4H), 6.71 (s, 2H, =CH), 3.55–3.25 (m, 4H, CH$_2$ bridge), 2.44 (s, 6H, Me). $^{13}$C NMR (CD$_2$Cl$_2$): δ 137.1 (C), 130.3 (C), 128.1 (C), 126.3 (CH), 125.8 (CH), 125.3 (CH), 123.6 (CH), 116.6 (C-Me), 101.0 (CH), 28.9 ( CH$_2$-bridge), 11.79 (Me).

SYNTHESIS 4
Rac- AND meso-1,2-ETHYLENE-BIS(1-METHYL2-INDENYL) ZIRCONIUM DIMETHYL 20 mg of rac- and 20 mg of meso-1,2-ethylene-bis(1-methyl-2-indenyl)zirconium dichloride, obtained as described in Synthesis 3, were separately suspended in 1 ml of C$_6$D$_6$, in different NMR tubes. About 5 mg of MeLi in excess, in the form of a white powder, were added to each NMR tube in the drybox. Occasional shaking of the NMR tube gave within 2 hours clean conversion to the corresponding rac- and meso-1,2-ethylene-bis(1-metlyl-2-indenyl) zirconium dimethyl isomers.

Rac-isomer:

$^1$H NMR (C$_6$D$_6$): δ 7.45–7.30 (m, 4H), 6.98–6.85 (m, 4H), 5.50 (s, 2H, =CH), 2.63–2.3 (m, 4H, CH$_2$ bridge), 2.09 (s, 6H, Me), −1.02 (s, 6H, Zr-Me). 13C NMR (C$_6$D$_6$): δ 129.6 (C), 125.2 (CH), 124.8 (C), 123.4 (CH), 122.6 (CH), 110.0 (5 ring C-Me), 97.6 (5-ring CH), 40.1 (Zr-Me), 26.8 (CH$_2$-bridge), 10.8 (Me).

Meso-isomer:

$^1$H NMR (C$_6$D$_6$): δ 7.42 (d, 2H), 7.30 (d, 2H), 7.04 (t, 2H), 6.9 (t, 2H), 5.93 (s, 2H, =CH), 2.6–2.3 (m, 4H, CH$_2$ bridge), 2.03 (s, 6H, Me), −0.38 (s, 3H, Zr-Me), −1.82 (s, 3H, Zr-Me). 13C NMR (C$_6$D$_6$): δ 129.2, 127.4, 125.6, 125.0, 123.7, 123.2, 121.9, 108.6 (5 ring (C-Me), 97.8 (5 ring CH), 44.1 (Zr-Me), 37.0 (Zr-Me), 27.5 (CH$_2$-bridge), 11.6 (Me).

SYNTHESIS 5
Rac- AND meso-1,2-ETHYLENE-BIS(1-ETHYL-2-INDENYL) ZIRCONIUM DICHLORIDE (a) Preparation of the ligand 1,2-bis(1-ethyl-2-indenyl) ethane 1.36 g, 5.26 mmol of 1,2-bis(2-indenyl)ethane, prepared as described in the above reported Synthesis 1(a), were dissolved in 25 mL THF and cooled to −10° C. 5.5 ml of a 1.6 M solution of BuLi in hexane (8.8 mmoles) were added and the resulting orange/brown solution was stirred for 2 hours, at room temperature. To the obtained ;mixture was added, by means of a cannula, a solution of 1.1 ml of EtI (7.1 mmol) in 10 ml THF, at −10° C. After 2 hours, the THF was removed under vacuum, and Et$_2$O was added. The thus obtained ether solution was washed 3 times with a saturated solution of NaHCO$_3$ and 3 times with a saturated aqueous solution of NaCl. After drying over MgSO$_4$, 1.46 g of 1,2-bis(1-ethyl-2-indenyl)ethane was isolated, in the form of a yellow oil. $^1$H NMR and GC showed that it consisted of the three possible double bond isomers.

(b) Preparation of the zirconocene 4.5 ml of a 1.6 M solution of n-BuLi in hexane (7.2 mmol) were added to a suspension of 1.16 g (3.5 nmmoles) of 1,2-bis(1-ethyl-2-indenyl)ethane, obtained as described above, in 50 ml of Et$_2$O, at −10° C. The mixture was maintained under stirring for 45 minutes and Et$_2$O was removed in vacuum; the thus obtained dianion was suspended in 80 ml of toluene, at 20° C. in a drybox. A slurry of 1.16 g (4.93 mmoles) of ZrCl$_4$ in 10 ml of toluene was added to the reaction mixture, which turned from yellow to dark brown. After stirring for 21 hours, at 20° C., the toluene solution was separated by centrifugation and the remaining solid was extracted with toluene (3×25 ml). The toluene extracts were combined, concentrated and crystallized at −35° C., thus giving 72 mg of rac-1,2-ethylene-bis(1-ethyl-2-indenyl)zirconium dichloride.

The toluene-insoluble precipitate, obtained from the reaction mixture, was extracted with CH$_2$Cl$_2$; after removal of the CH$_2$Cl$_2$ in vacuum, a yellow powder was obtained, which was washed with pentane (2×5 ml) to give 300 mg of pure meso-1,2-ethylene-bis 1-ethyl-2-indenyl)zirconium dichloride.

Rac-isomer:
$^1$H NMR (d$^8$-THF): δ 7.42 (d, 2H), 7.3 (d, 2H), 7.06 −6.94 (m, 4H), 6.23 (s, 2H, =CH), 3.62–3.50 (m, 4H, CH$_2$ bridge), 3.4–2.93 (m, 2H, CH$_2$ bridge), 2.88 (dq, 2H), 1.06 (t, 6H, Me). $^{13}$C NMR (d$^8$-THF): δ 137.0 (C), 130.0 (C), 128.0 (C), 127.0 (CH), 126.0 (CH), 125.5 (CH), 124.0 (CH), 122.8 (C-Me), 98.0 (CH), 27.0 (CH$_2$-bridge), 20.7 (CH$_2$), 16.0 (Me).

Meso-isomer:
$^1$H NMR (CD$_2$Cl$_2$): δ 7.51(m, 2H), 7.37 (m, 2H), 7.20–7.07 (m, 4H), 6.73 (s, 2H, =CH), 3.50–3.28 (m, 4H, CH$_2$ bridge), 3.12–3.00 (dq, 2H), 2.81–2.69 (dq, 2H) 1.14 (t, 6H, Me). $^{13}$C NMR (CD$_2$Cl$_2$): δ 135.0 (C), 129.9 (C), 125.6 (C), 125.0 (CH), 124.3 (CH), 123.0 (CH), 122.9 (CH), 122.1 (C-Me), 100.8 (CH), 28.9 (CH$_2$-bridge), 20.0 (CH$_2$), 11.8 (Me).

SYNTHESIS 6
Meso-1,2-ETHYLENE-BIS(1-ETHYL-2-INDENYL) ZIRCONIUM DIMETHYL 20 mg of meso-1,2-ethylene-bis(1-ethyl-2-indenyl) zirconium dichloride, prepared as described in the above reported Synthesis 5, were suspended in 1 ml of C$_6$D$_6$ in a NMR tube. About 5 mg of MeLi in excess, in the form of a white powder, were added in the drybox. Occasional shaking of the NMR tube gave within 2 hours the final product meso-1,2-ethylene-bis(1-ethyl-2-indenyl)zirconium dimethyl.

$^1$H NMR (C$_6$D$_6$): δ 7.42 (d, 2H), 7.30 (d, 2H), 7.04 (t, 2H), 6.9 (t, 2H), 5.95 (s, 2H, =CH), 2.8–2.2 (m, 4H, CH$_2$ bridge+m, 4H, CH$_2$Me), 1.0 (t, 6H, Me), −0.4 (s, 3H, Zr-Me), −1.9 (s, 3H, Zr-Me).

SYNTHESIS 7
1,2-ETHYLENE-BIS(1,3-DIMETHYL-2-INDENYL) ZIRCONIUM DICHLORIDE (a) Preparation of the ligand 1,2-bis(1,3-dimethyl-2-indenyl)ethane Preparation of 1,2-bis(1-methyl-2-indenyl)-ethane

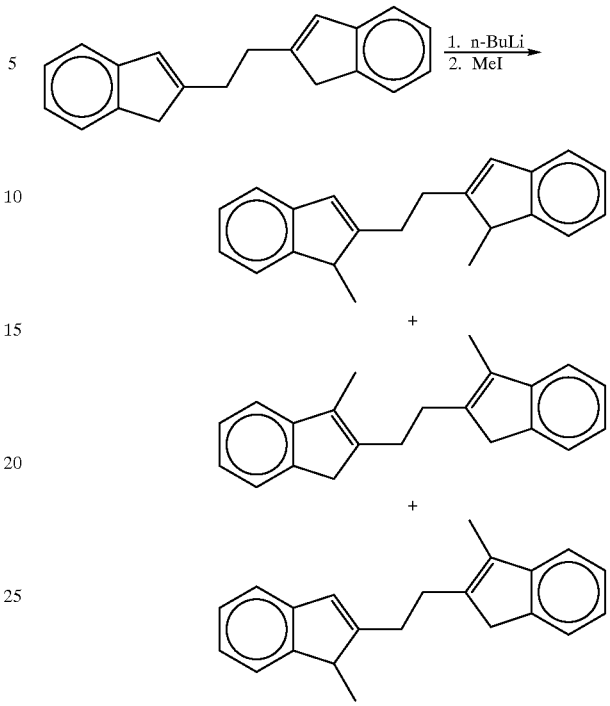

10 g (38.7 mmoles) of 1,2-bis(2-indenyl)ethane, prepared as described in the above Synthesis 1(a), were suspended in 100 mL THF and to the obtained mixture were added 32 mL n-BuLi (2.5 M solution in hexane), during 15 minutes, at 0° C. The resulting solution was allowed to warm to 20° C. and maintained under stirring for 30 minutes at 20° C.; to the thus obtained red/brown solution, previously cooled to 0° C., were then added, over a few minutes, 6.0 mL MeI in 50 mL THF (also previously cooled to 0° C.). The reaction mixture was allowed to warm to 20° C. and was maintained under stirring for 2 hours. Subsequently, the solvent were removed in vacuum. The thus obtained sticky yellow/orange solid was dissolved in 200 mL Et$_2$O and extracted 3 times with a saturated aqueous solution of NaHCO$_3$ and a saturated solution of NaCl. The aqueous and organic layers were separated and Et$_2$O was removed in vacuum, thus yielding 9.7 g (yield of 88%) of 1,2-bis(1-methyl-2-indenyl)ethane. This product consisted of a mixture of the 3 isomers reported above, wherein the double bond isomeric moieties I and II, reported below, are formed in a ratio of about 1:10 (confirmed by $^1$H-NMR analysis):

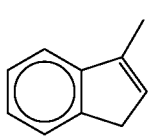

I

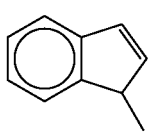

II $^1$H NMR (CDCl$_3$): δ 1.36 (d, J=7.5 Hz, 6H, CH$_3$ (isomer II)), 2.09 (s, 6H, CH$_3$ (isomer I)), 2.60–2.90 (m, 4H, CH$_2$-bridge), 3.30–3.43 (s, 4H (isomer I) and d, 2H (isomer II)), 6.53 (s, 2H, =CH 5-ring), 7.10–7.45 (m, 8H, aromatic H) ppm.

Preparation of 1,2-bis(1,3-dimethyl-2-indenyl)ethane 1,2-Bis(1-methyl-2-indenyl)ethane (9.7 g, 33.9 mmol), obtained as described above, was suspended in 100 mL THF and to the obtained mixture were added 28.5 mL n-BuLi (in the form of a 2.5M hexane solution), over a period of 10 minutes, at 0° C. The reaction mixture was allowed to warm to 20° C. and maintained under stirring for 90 minutes, at 20° C.; to the thus obtained red/brown solution, previously cooled to 0° C., were added, over few minutes, 5.3 mL MeI in 50 mL THF (also previously cooled to 0° C.). The reaction mixture was allowed to warm to 20° C. and was maintained under stirring for 2 hours. After removal of the solvent in vacuum, the thus obtained sticky yellow/orange solid was dissolved in 200 mL Et$_2$O and extracted 3 times with a saturated aqueous solution of NaHCO$_3$ and a saturated aqueous solution of NaCl. The aqueous and organic layers were separated and Et$_2$O was removed in vacuum; the resulting yellow sticky solid was washed with hexane, to give 2.3 g of 1,2-bis(1,3-methyl-2-indenyl)ethane (24% yield).

(b) Preparation of the zirconocene

Preparation of the dianion of 1,2-bis(1,3-dimethyl-2-indenyl)ethane 1.47 g (4.68 mmol) of 1,2-bis(1,3-dimethyl-2-indenyl) ethane were dissolved in 30 mL Et$_2$O and to the obtained solution were added 3.9 mL n-BuLi (as a solution 2.5 M in hexane), at −78° C., over a period of 5 minutes. The reaction mixture was maintained under stirring for 30 minutes, at −78° C., and then was allowed to warm to 20° C. A precipitate formed during the reaction. The thus obtained orange/brown reaction mixture was filtered and the solid was washed with 20 ml hexane, in order to remove 1,1'-dimethylated products, thus giving the dianion of 1,2-bis(1, 3-dimethyl-2-indenyl)ethane, in the form of a white/yellow solid, which was used without further purification for the subsequent reaction with ZrCl$_4$, as described below.

$^1$H NMR (d$^8$-THF): δ 2.43 (s, 12H, CH$_3$), 3.01 (s, 4H, CH$_2$ bridge), 6.25 (m, 4H, aromatic H), 7.03 (m, 4H, aromatic H) ppm.

Preparation of 1,2-ethylene-bis(1,3-dimethyl-2-indenyl) zirconium dichloride

The dianion of 1,2-bis(1,3-dimethyl-2-indenyl)ethane, obtained as described above, was suspended in 30 mL toluene and to the obtained mixture was added, at −30° C., over a period of few minutes, a suspension of 0.95 g (4.08 mmol) of ZrCl$_4$ in 10 ml toluene.

The reaction mixture was allowed to warm to 20° C. and the color changed to orange. The mixture was maintained under stirring overnight and was subsequently filtered; the obtained solid was extracted with toluene (3×10 ml). After removal of the solvent in vacuum, the obtained solid was washed with hexane, to afford 206 mg of 1,2-ethylene-bis (1,3-dimethyl-2-indenyl)zirconium dichloride, as an orange powder.

$^1$H NMR (CD$_2$Cl$_2$): δ 2.59 (s, 12H, CH$_3$), 3.50 (s, 4H, CH$_2$ bridge), 7.16 (m, 4H, aromatic H), 7.45 (m, 4H, aromatic H) ppm.

SYNTHESIS 8

Rac- AND meso-1,2-ETHYLENE-BIS(4-PHENYL-2-INDENYL) ZIRCONIUM DICHLORIDE (a) Preparation of the ligand 1,2-bis(4-phenyl-2-indenyl) ethane This ligand was prepared through the intermediate 2,5-bis(2-phenyl-benzyl) adipic acid diethylester, synthesized according to the following reaction scheme:

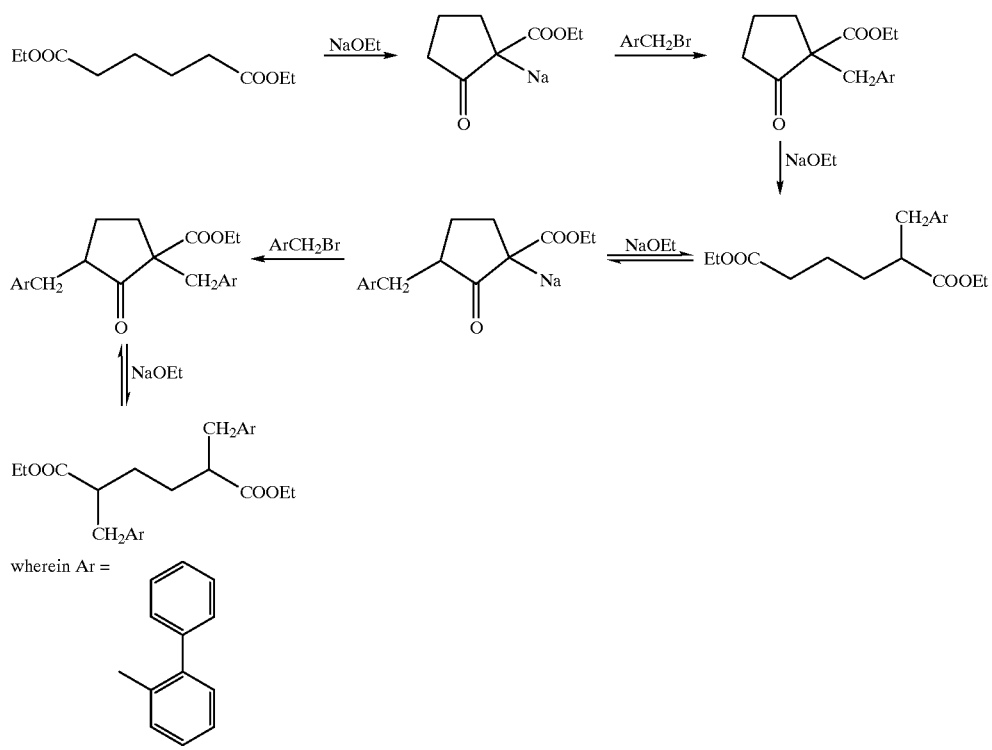

Into a 3 neck flask, equipped with water cooler, were added 43.8 mL (0.22 mol) of diethyladipate and 220 mL THF. 16.3 g (0.24 mol, 1.1 equivalents) of NaOEt were added in small portions, at 20° C., and the reaction mixture was stirred at 60° C. for 16 hours. After cooling to 20° C., 48.6 g (0.20 mol) of 2-phenyl-benzyl bromide was added dropwise. The reaction mixture was stirred at 60° C., for 16 hours, to give 2-(2-phenyl-benzyl) adipic acid diethylester as a viscous oil, in a yield of 92%.

$^1$H NMR (CDCl$_3$): δ 1.08 (t, 3H, CH$_3$), 1.21 (t, 3H, CH$_3$), 1.28–1.45 (q, 2H, CH$_2$ and m, 2H, CH$_2$), 2.11 (t, 2H, CH$_2$), 2.37 (m, 1H, CH), 2.85 (d, 2H, CH$_2$), 3.97 (q, 2H, CH$_2$), 4.08 (q, 2H, CH$_2$), 7.16–7.48 (m, 9H, CH) ppm.

$^{13}$C NMR (CDCl$_3$): δ 14.05 (CH$_2$Me), 14.17 (CH$_2$Me), 22.41 (CH$_2$), 31.39 (CH$_2$), 33.86 (CH$_2$), 35.60 (CH$_2$), 46.01 (CH), 60.03 (CH$_2$CH$_3$), 60.14 (CH$_2$CH$_3$), 126.28 (CH), 126.90 (CH), 127.23 (CH), 128.11 (CH), 129.12 (CH), 129.71 (CH), 130.08 (CH), 136.62 (C), 141.56 (C), 142.24 (C), 173.13 (CO$_2$Et), 175.22 (CO$_2$Et).

Under the operating conditions reported above, to the obtained diethylester were sequentially added 14.9 g (0.22 mol) of NaOEt and 44.4 g (0.18 mol) of 2-phenyl-benzyl bromide; the obtained mixture was stirred for 16 hours, at 60° C. After the addition of dilute HCl to neutralize the base, the THF and the aqueous acidic phases were separated. The aqueous acidic layer was extracted 3 times with CH$_2$Cl$_2$. The combined THF and CH$_2$Cl$_2$ extracts were evaporated to dryness, to give the intermediate 2,5-bis(2-phenyl-benzyl) adipic acid diethylester, in the form of a very viscous oil.

Said intermediate 2,5-bis(2-phenyl-benzyl) adipic acid diethylester was then reacted according to the following reaction scheme:

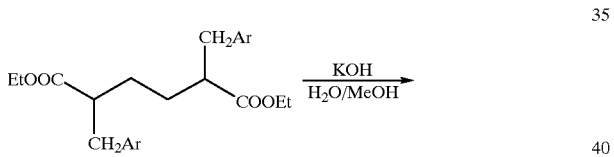

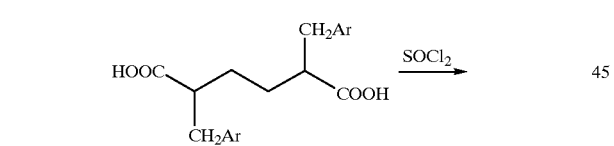

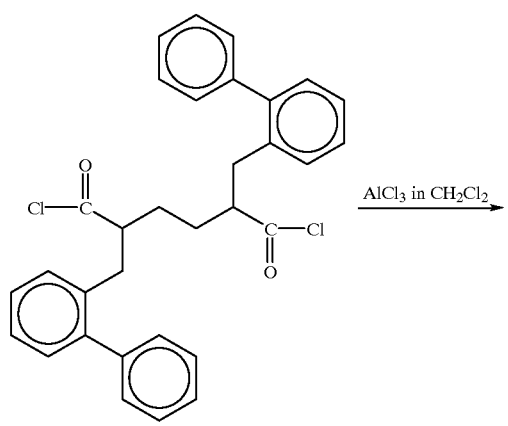

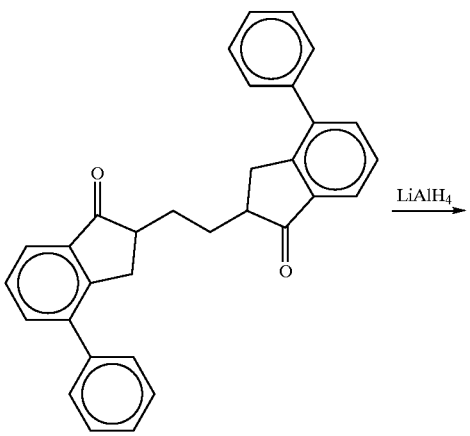

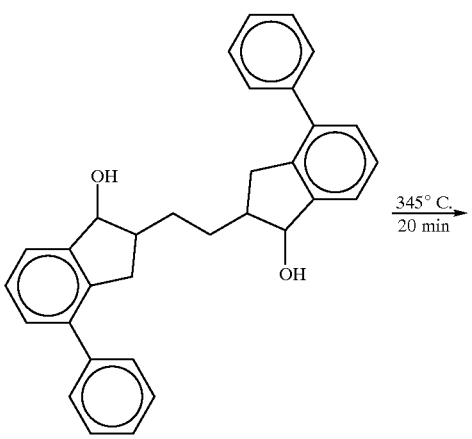

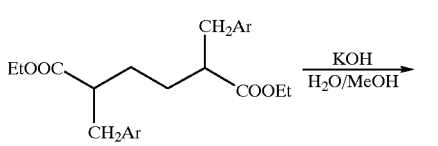

To the 2,5-bis(2-phenyl-benzyl) adipic acid diethylester, obtained as described above, were added 180 mL of a solution of 6 M KOH in H$_2$O/MeOH and the reaction mixture was refluxed for 16 hours. MeOH was removed on a rotary evaporator and the aqueous layer was washed with Et$_2$O (2×200 mL). The alkaline aqueous layer was acidified, at 0° C., with HCl 37% to pH 1. A white/yellow powder was formed, filtered off and washed with water and a little hexane. Said powder was thoroughly dried, to afford 77.0 g of 2,5-bis(2-phenyl-benzyl) adipic acid (85% yield).

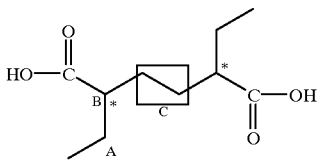

$^1$H NMR (d$_8$-THF): δ 1.00–1.30 (m, 4H, CH$_2$), 2.22 (m, 2H, CH), 2.60 (m, 2H, CH$_2$), 2.76 (m, 2H, CH$_2$), 7.05–7.39 (m, 18H, CH), 10.45 (s, 2H, OH) ppm.

$^{13}$C NMR (d$_8$-THF): δ 30.81 (CH$_2$;C), 36.18 (CH$_2$; A), 36.34 (CH$_2$*;A), 47.04 (CH; B), 47.24 (CH*;B), 127.02 (CH), 127.88 (CH), 128.20 (CH), 129.15 (2×CH), 130.37 (2×CH), 130.77 (CH), 131.00 (CH), 138.49 (C), 143.20 (C), 143.68 (C), 176.50 (CO$_2$H) ppm.

In a 1 L flask equipped with a reflux condenser, containing 77.0 g (0.16 mol) of 2,5-bis(2-phenyl-benzyl) adipic acid, obtained as described above, were added 150 mL (2.06 mol) of SOCl$_2$). A white suspension was obtained, which was warmed to 50° C. and became a yellow solution, with concomitant evolution of HCl and SO$_2$. After gas evolution had finished, the excess SOCl$_2$ was removed under vacuum. To the obtained mixture were then added 100 mL of toluene, which was subsequently removed under vacuum to ensure complete removal of SOCl$_2$. 2,5-bis(2-phenyl-benzyl) adipic acid dichloride (82.9 g, yield of 100%) was isolated, in the form of a viscous beige oil.

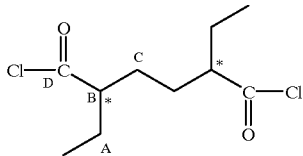

$^1$H NMR (CDCl$_3$): δ 1.17 (m, 2H, CH$_2$), 1.36 (m, 2H, CH$_2$), 2.64 (m, 2H, CH), 2.85 (dd, 2H, CH$_2$), 3.07 (m, 2H, CH$_2$), 7.20–7.55 (m, 18H, aromatic. CH) ppm.

$^{13}$C NMR (CDCl$_3$): δ 28.39 (CH$_2$;C), 35.06 (CH$_2$; A), 35.14 (CH$_2$*;A), 57.28 (CH; B), 57.46 (CH*;B), 127.22 (CH), 127.41 (CH), 127.80 (aromatic. CH), 128.56 (2×CH), 129.14 (2×CH), 129.94 (CH), 130.53 (CH), 134.58 (C), 141.11 (C), 142.29 (C), 175.89 (COCl; D), 175.93 (COCl*;D) ppm.

To a suspension of 56.0 g (0.42 mol) of AlCl$_3$ in 40 mL CH$_2$Cl$_2$, under nitrogen, was added at 20° C., 82.9 g (0.16 mol) of 2,5-bis(2-phenyl-benzyl) adipic acid dichloride, obtained as described above, diluted in 250 mL CH$_2$Cl$_2$ (1.3 eq. AlCl$_3$ per acid chloride group). After addition was completed, the reaction mixture was maintained under stirring for 5 minutes and then poured onto ice. CH$_2$Cl$_2$ was separated from the water layer and the water layer was extracted with 2×200 mL CH$_2$Cl$_2$. The combined CH$_2$Cl$_2$ layers were washed with a saturated solution of NaHCO$_3$. CH$_2$Cl$_2$ was removed under vacuum and the resulting powder was washed with a little hexane, to give 63.3 g of the 1,2-bis(4-phenyl-indanonyl)ethane (89% yield).

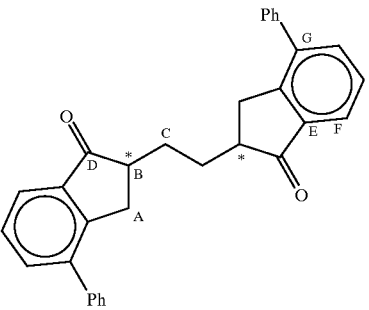

$^1$H NMR (CDCl$_3$): δ 1.55 (m, 2H, CH$_2$), 2.07 (m, 2H, CH$_2$), 2.63 (m, 2H, CH$_2$), 2.86 (m, 2H, CH), 3.36 (dd, 2H, CH$_2$, J=18 Hz), 7.10–7.86 (m, 16H, aromatic. CH) ppm. 13C NMR (CDCl$_3$): δ 28.60 (CH$_2$; C), 29.51 (CH$_2$*;C), 32.44 (CH$_2$; A), 32.75 (CH$_2$*;A), 47.19 (CH; B), 47.82 (CH*;B), 122.77 (CH; F), 122.84 (CH*;F), 127.67 (CH), 127.97 (CH), 128.42 (2×CH), 128.62 (2×CH), 134.86 (CH), 137.04 (C; G), 137.10 (C*;G), 138.99 (C), 140.25 (C; E), 140.27 (C*;E), 151.01 (C), 208.32 (C=O; D), 208.42 (C=O*;D) ppm.

20.0 g (0.045 mol) of 1,2-bis(4-phenyl-indanonyl)ethane, obtained as described above, were dissolved in 310 mL of dry THF, and the obtained solution was slowly added, over a period of 20 minutes, via a cannula, to a suspension of 1.85 g (0.049 mol, 1.09 eq.) of LiAlH$_4$ in 80 mL THF, contained in a 1L round-bottom flask, previously cooled to 0° C. At the end of the addition, the reaction mixture was maintained under stirring for 45 minutes, at 20° C. THF was removed under vacuum and, after the addition of ice and diluted HCl, the resulting suspension was acidified to pH 1. The thus obtained mixture was then filtered, to give 1,2-bis(4-phenyl-2-indanolyl)ethane, in the form of an off-white powder. After washing with water, the product was dried to give 18.3 g of 1,2-bis(4-phenyl-2-indanolyl)ethane (yield 91%).

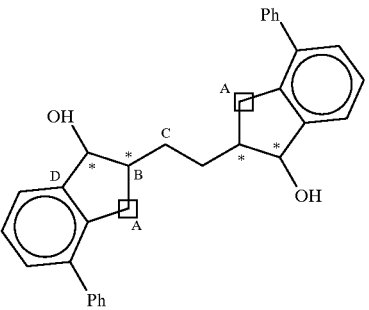

$^1$H-NMR (CDCl$_3$): δ 1.40–2.22 (m, 8H, 3×CH$_2$, 2×OH), 2.55 (m, 2H, CH), 3.11 (dd, 2H, CH$_2$, J=18 Hz), 4.85 (m, 2H, CH—OH), 7.10–7.50 (16H, aromatic. CH) ppm. $^{13}$C-NMR (d$_8$-THF): δ 33.20 (CH$_2$; C), 33.38 (CH$_2$*;C), 37.04 (CH$_2$; A), 52.64 (CH; B), 52.86 (CH*;B), 81.94 (C—OH), 123.80 (CH), 127.84 (2×CH), 128.44 (CH), 129.30 (2×CH), 129.64 (2×CH), 139.22 (CH), 140.06 (C), 142.34 (C), 148.96 (C; D), 149.03 (CH*;D).

11.0 g (0.025 mol) of 1,2-bis(4-phenyl-2-indanolyl) ethane, obtained as described above, were put into a 1 L 3-neck round-bottom flask and heated to 345° C., for 20 minutes, under a slow steam of N$_2$. After cooling, a yellow glass was obtained, which was dissolved in CH$_2$Cl$_2$. After removal of the CH$_2$Cl$_2$ under vacuum, 8.8 g of 1,2-bis(4-phenyl-2-indenyl)ethane (87% yield) were isolated, in the form of a yellow powder consisting of a mixture of two double-bond isomers.

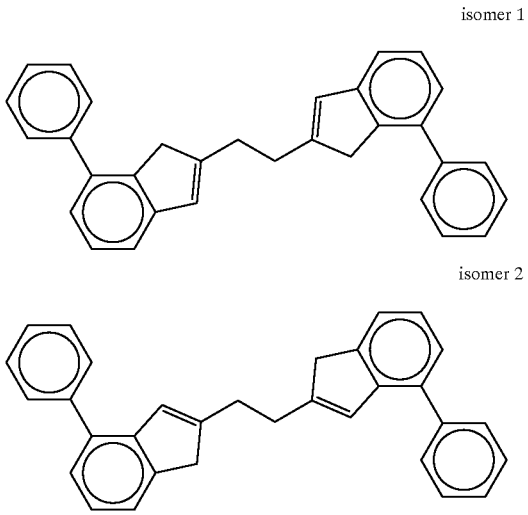

Isomer 1:
¹H NMR (CDCl₃): δ 2.82 (s, 4H, CH₂), 3.46 (s, 4H, CH₂), 6.64 (s, 2H, CH), 7.14–7.59 (m, 16H, CH) ppm. ¹³C NMR (CDCl₃): δ 30.57 (CH₂), 41.11 (CH₂), 119.25 (CH), 124.47 (CH), 126.73 (CH), 127.02 (2×CH), 128.37 (2×CH), 137.48 (C), 140.46 (C), 141.23 (C), 145.96 (C), 149.90 (q, C 5-ring) ppm.

Isomer 2:
¹H NMR (CDCl₃): δ 2.82 (s, 4H, CH₂), 3.46 (s, 4H, CH₂), 6.76 (s, 2H, CH), 7.14–7.59 (m, 16H, (CH) ppm. ¹³C NMR (CDCl₃): δ 30.69 (CH₂), 41.32 (CH₂), 119.25 (CH), 122.43 (CH), 124.09 (CH), 128.61 (2×CH), 128.81 (2×CH), 134.23 (C), 141.00 (C), 143.06 (C), 143.63 (C), 150.11 (q, C 5-ring) ppm.

(b) Preparation of the zirconocene 465 mg, 1.13 nmmol of 1,2-bis(4-phenyl-2-indenyl) ethane, prepared as described above, were dissolved in 20 mL Et₂O, in a Schlenk tube, and cooled to –78° C. 0.95 mL of n-BuLi as a solution 2.5 M in hexane (2.38 mmol; 2.1 equiv.) was added dropwise. The reaction mixture was allowed to warm to 20° C. Et₂O was removed under vacuum, to afford the dianion, in the form of a light-yellow powder.

¹H NMR (d₈-THF): δ 3.22 (s, 4H, CH₂), 5.85 (ds, 2H, CH), 6.08 (ds, 2H, CH), 6.35 (m, 4H, aromatic CH), 7.08 (m, 4H, aromatic CH), 7.28 (t, 4H, aromatic CH), 7.74 (d, 4H, arom. CH) ppm.

The above obtained dianion was suspended in toluene and cooled to –20° C.; to the obtained mixture were added 0.28 g (1.19 mmol; 1.05 equivalents) of ZrCl₄. The reaction mixture was maintained under stirring for 16 hours, at 20° C.; then it was centrifuged and the toluene layer was discarded. The remaining powder was washed with toluene (20 mL) and then extracted with CH₂Cl₂, in order to separate the product from LiCl. A pure mixture of rac and meso-isomers of 1,2-ethylene-bis(4-phenyl-2-indenyl)zirconium dichloride was obtained, in the form of a yellow powder. By crystallization from toluene, the meso isomer could be completely separated from the rac-isomer. The rac-isomer was obtained as a rac:meso mixture of about 4:1.

Rac-isomer:
¹H NMR (C₆D₆): δ 2.48 (ds, 4H, CH₂-bridge), 5.53 (ds, 2H, CH, J=2.1 Hz), 6.37 (ds, 2H, CH, J=2.1 Hz), 6.90–7.70 (m, 16H, arom. CH) ppm. ¹H NMR (CD₂Cl₂): δ 3.39 (m, 4H, CH₂-bridge), 6.35 (ds, 2H, CH, J=2.1 Hz), 6.70 (ds, 2H, CH, J=2.1 Hz), 7.22–7.76 (m, 16H, arom. CH) ppm. ¹³C NMR (CD₂Cl₂): δ 30.81 (CH₂), 100.38 (CH), 103.94 (CH), 124.52, 125.89, 126.19, 127.65, 128.55, 129.15, 130.30, 139.58, 140.36, 140.51 ppm.

Meso-isomer:
¹H NMR (C₆D₆): δ 2.41 (m, 4H, CH₂-bridge), 5.95 (ds, 2H, CH, J=2.1 Hz), 6.39 (ds, 2H, CH, J=2.1 Hz), 6.85–7.62 (m, 16H, arom. CH) ppm. ¹H NMR (CD₂Cl₂): δ 3.37 (s, 4H, CH₂-bridge), 6.41 (ds 2H, CH, J=2.1 Hz), 6.78 (ds, 2H, CH, J=2.1 Hz), 7.19–7.64 (m, 16H, arom. CH) ppm. ¹³C NMR (CD₂Cl₂): δ 30.63 (CH₂), 101.28 (CH), 105.85 (CH), 139.57, 139.58, 139.70 ppm.

SYNTHESIS 9
Meso-1,2-ETHYLENE-BIS(4-PHENYL-2-INDENYL) ZIRCONIUM DIMETHYL

Meso-1,2-Ethylene-bis(4-phenyl-2-indenyl)zirconium dichloride, obtained as described in the above Synthesis 9, were suspended in C₆D₆ and MeLi in excess was added; after 30 minutes at 20° C., meso-1,2-ethylene-bis(4-phenyl-2-indenyl)zirconium dimethyl was obtained.

¹H NMR (C₆D₆): δ –1.83 (s, 3H, CH₃), 0.28 (s, 3H, CH₃), 2.28 (ds, 4H, CH₂-bridge, J=4.5 Hz), 5.90 (ds, 2H, CH, J=2.1 Hz), 6.24 (ds, 2H, CH, J=2.1 Hz), 6.89–7.48 (m, 16H, arom. CH) ppm.

SYNTHESIS 10
Rac- AND meso-1,2-ETHYLENE-BIS(1-METHYL-4-PHENYL-2-INDENYL) ZIRCONIUM DICHLORIDE (a) Preparation of the ligand 1,2-bis(1-methyl-4-phenyl-2-indenyl)ethane The ligand was prepared according to the following reaction scheme:

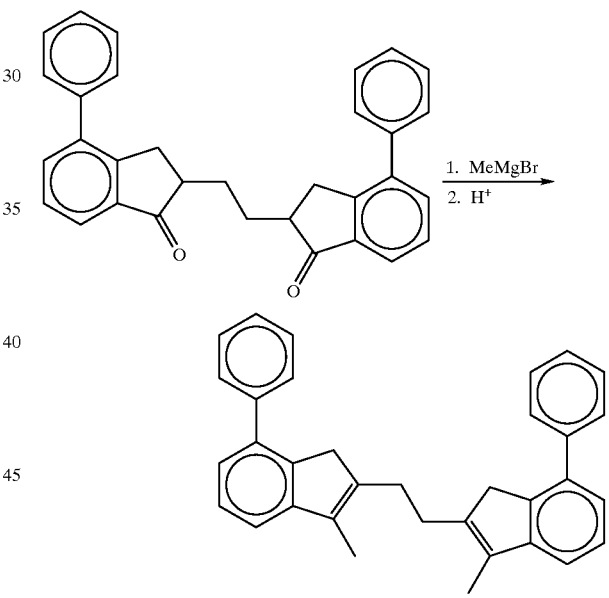

To a solution of 67.8 mL MeMgBr (3M in ether) in 100 MnL Et₂O was added a solution of 15 g (33.9 mmol) of 1,2-bis(4-phenyl-indanonyl)ethane, prepared as described in the above synthesis 8(a), in 150 mL THF, over a period of 45 minutes, at 0° C. The formation of a white/beige precipitate was observed. The reaction mixture was allowed to warm to 20° C. and was maintained under stirring for 2 hours. The reaction mixture was then poured into ice and acidified to pH 1, with 37% HCl, and finally extracted with Et₂O. The organic layer was extracted with a saturated solution of NaCl and the solvent was removed in vacuum. The formed diol was dissolved in CH₂Cl₂ and p-toluenesulfonic acid was added. The mixture was stirred overnight at 20° C. The solution was dried over MgSO₄, filtered and the solvent was removed in vacuum, thus yielding 9.0 g of the ligand 1,2-bis(1-methyl-4-phenyl-2-indenyl)ethane (69% yield).

¹H NMR (CD₂Cl₂): δ 2.08 (s, 6H, CH₃), 2.69 (s, 4H, CH₂ bridge), 3.43 (ds, 4H, CH₂ 5-ring), 7.2–7.6 (m, 16H, aromatic H) ppm.

(b) Preparation of the zirconocene

To a solution of 0.54 g (1.23 mmol) of 1,2-bis(1-methyl-4-phenyl-2-indenyl)ethane, prepared as described above, in 20 mL Et₂O, was added 1.1 mL of n-BuLi (in the form of a 2.5M solution in hexane), at −78° C. The reaction mixture was allowed to warm to 20° C.; the formation of a precipitate was observed and the color changed to orange/red. The reaction mixture was stirred for 2 hours, at 20° C., and the solvent was removed in vacuum. The dianion was obtained in the form of a sticky product; after washing with hexane, the orange powder was suspended in 10 mL toluene and 0.29 g of ZrCl₄ were added, at −30° C. The reaction mixture was allowed to warm to 20° C. and was stirred overnight. The thus obtained orange suspension was filtered and the filtrate was concentrated and used for crystallization.

The crude product was 1,2-ethylene-bis(1-methyl-4-phenyl-2-indenyl)zirconium dichloride, as a mixture of rac/meso isomers in a 1:1 ratio. By successive crystallizations, it could be obtained as a 4:1 rac/meso mixture. Crystallization from dichloromethane/hexane mixture gave 94% pure meso-isomer.

Rac isomer:

¹H NMR (CD₂Cl₂): δ 2.34 (s, 6H, CH₃), 3.14–3.59 (m, 4H, CH₂ bridge, symmetric pattern), 6.44 (s, 2H, CH 5-ring), 7.10–7.70 (m, 16H, aromatic H) ppm.

Meso isomer:

¹H NMR (CD₂Cl₂): δ 2.48 (s, 6H, CH₃), 3.20–3.50 (m, 4H, CH₂ bridge, symmetric pattern), 6.90 (s, 2H, CH 5-ring), 7.10–7.70 (m, 16H, aromatic H) ppm.

SYNTHESIS 11

Rac- AND meso-1,2-ETHYLENE-BIS(1-ISOPROPYL-4-PHENYL-2-INDENYL) ZIRCONIUM DICHLORIDE (a) Preparation of the ligand 1,2-bis(1-isopropyl-4-phenyl-2-indenyl)ethane The ligand was prepared according to the following reaction scheme:

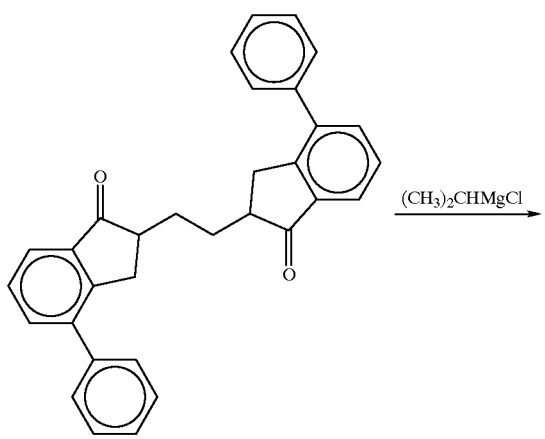

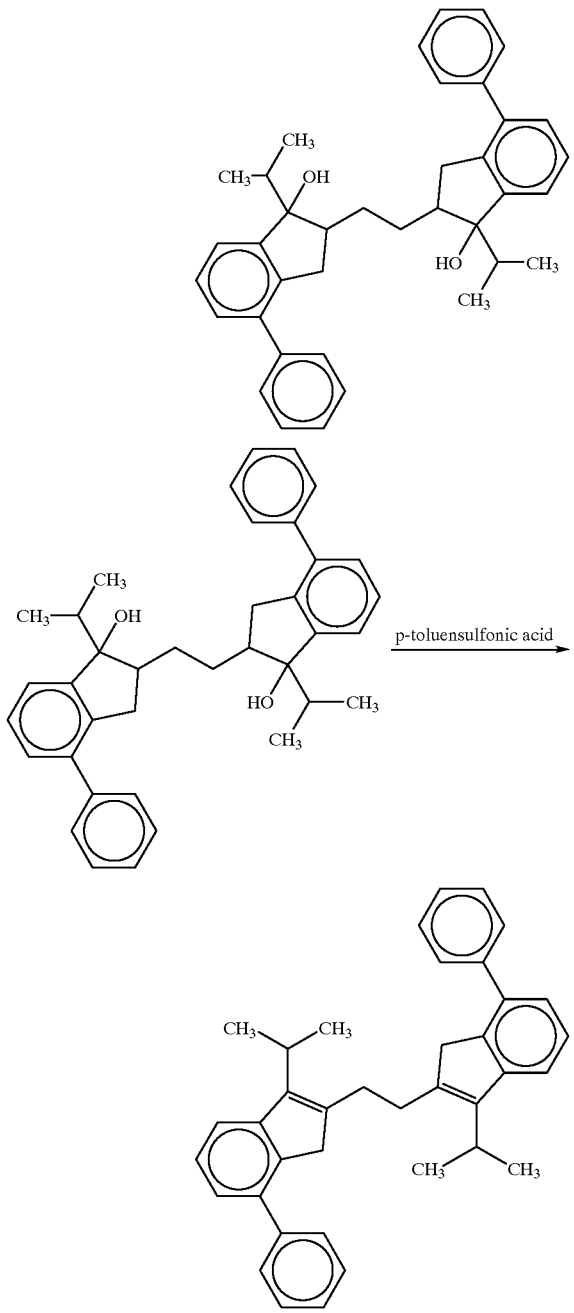

In a 250 mL flask, containing 40 mL of a solution 2.0 M of i-PrMgCl in Et₂O (9 equivalents), previously cooled to 0° C., was added dropwise, over a period of 15–20 minutes, a solution of 4 g of 1,2-bis(4-phenyl-indanonyl)ethane (9.17 mmol), prepared as described in the above synthesis 8(a), in 80 mL THF. The obtained mixture was stirred for 90 minutes and then poured onto ice. The organic layer was separated and the aqueous layer extracted with CH₂Cl₂. The combined organic layers were washed with a saturated solution of NaCl and then dried over MgSO₄, to give the diol. This product was dissolved in 100 ml of CH₂Cl₂ and to the obtained solution were added 1.5 g of p-toluensulfonic acid; the reaction mixture was maintained under stirring for 20 hours, at 20° C. The obtained mixture was dried with MgSO₄, to give a clear yellow solution, which was filtered through a plug of silica to give pure 1,2-bis(1-isopropyl-4-phenyl-2-indenyl)ethane.

$^1$H NMR (CDCl$_3$): δ 1.36 (d, 12H, CH$_3$), 2.67 (s, 4H, CH$_2$-brug), 3.18 (septet, 2H, CH), 3.36 (s, 4H, CH$_2$), 7.13–7.52 (m, 16H, arom. CH) ppm. $^{13}$C-NMR (CDCl$_3$): δ 21.13 (CH$_3$), 26.75 (CH), 29.34 (CH$_2$), 40.41 (CH$_2$), 119.47 (CH), 124.24 (CH), 126.48 (CH), 126.91 (CH), 128.30 (2×CH), 128.49 (2×CH), 137.60 (q. C 5-ring), 140.64 (C), 140.98 (C), 141.41 (C), 142 66 (C), 145.50 (q, C 5-ring) ppm.

(b) Preparation of the zirconocene 0.29 g (0.58 mmol) of 1,2-bis(1-isopropyl-4-phenyl-2-indenyl)ethane, prepared as described above, were dissolved in 30 mL Et$_2$O and cooled to −78° C. 0.5 mL of n-BuLi (in the form of a 2.5M solution in hexane) were added. The obtained yellow solution became brown-red and the reaction mixture was allowed to warm to 20° C. The reaction mixture was stirred for 1 hour at 20° C. and Et$_2$O was removed in vacuum to give the dianion.

$^1$H NMR (d$^8$-THF): δ 1.4 (d, 12H, Me), 3.22 (s, 4H, bridge CH$_2$), 3.4 (septet, 2H, CHMe$_2$), 5.93 (s, 2H, CH), 6.28 (m, 4H, aromatic CH), 7.08 (t, 2H, aromatic CH), 7.22 (t, 2H, aromatic CH), 7.28 (t, 4H, aromatic CH), 7.66 (d, 4H, aromatic CH) ppm. The dianion was suspended in toluene and cooled to −30° C.; 0.15 g of ZrCl$_4$ (0.64 mmol) were added and the reaction niixture was stirred for 4 hours at 20° C. and then centrifuged. Toluene was discarded and the remaining powder was extracted with CH$_2$Cl$_2$. Centrifugation afforded a mixture of the two isomers rec/meso-1,2-ethylene-bis(1-isopropyl-4-phenyl-2-indenyl)zirconium dichloride, about in a 1:1 ratio.

First isomer: $^1$H NMR (C$_6$D$_6$): δ 1.15 (d, 6H, Me), 1.58 (d, 6H, Me), 2.5 (m, 2H, bridge), 2.92 (m, 2H, bridge), 3.35 (septet, 2H, CHMe$_2$), 6.69 (s, 1H, CH), 6.9–7.7 (m, 16H, aromatics) ppm.

Second isomer: $^1$H NMR (C$_6$D$_6$): δ 1.03 (d, 6H, Me), 1.09 (d, 6H, Me), 2.5 (m, 2H, bridge), 3.08 (m, 2H, bridge), 3.2 (septet, 2H, CHMe$_2$), 6.33 (s, 1H, CH), 6.9–7.7 (m, 16H, aromatics) ppm.

COMPARATIVE SYNTHESIS 1
Rac-1,2-ETHYLENE-BIS(1-INDENYL)ZIRCONIUM DICHLORIDE (EBIZrCl$_2$)

This zirconocene was prepared as described in the European patent application EP 0 575 875 (stages (a) and (b) of the synthesis of ethylene-bis(4,5,6,7-tetrahydroindenyl) zirconium dichloride).

COMPARATIVE SYNTHESIS 2
METHYLENE-BIS(2-INDENYL)ZIRCONIUM DICHLORIDE (a) Preparation of the ligand bis(2-indenyl)methane 44.3 g (335 mmol) of 1-indanone, 14.3 g (477 mmol) of paraformaldehyde and 38.4 g (471 mmol) of Me$_2$NH.HCl were combined in 105 ml absolute EtOH and 25 drops of 37% HCl added. This was refluxed for 2.5 hours. After allowing to cool to room temperature, a copious crystalline white precipitate formed. This was filtered off and washed with hexane to give 52.2 g (69%) of the Mannich base 2-CH$_2$N(CH$_3$)$_2$.HCl-1-indanone.

$^1$H NMR (CDCl$_3$): δ 9.9 (broad s, 1H, HCl), 7.73 (d, 1H), 7.62 (t, 1H), 7.5 (d, 1H), 7.38 (t, 1H), 3.8–3.2 (m, 5H), 2.95 (d, 3H, Me), 2.9 (d, 3H, Me). $^{13}$C NMR (CD$_2$Cl$_2$): δ 206.0 (CO), 154.9 (C), 136.6(CH), 135.0 (C), 128.1 (CH), 127.0 (CH), 124.3 (CH), 58.9 (CH$_2$), 44.0 (NMe$_2$), 34.6 (CH), 32.9 (CH$_2$).

52.2 g (232 mmol) of the Mannich base, prepared as described above, 43.2 g (327 mmol, 1.4 equivalents) of 1-indanone and 18.2 g (325 mmol, 1.4 equivalents) of KOH were placed in a 250 ml round-bottom flask and 200 ml toluene added. This was brought to reflux whereupon the color changed from yellow to a light purple. After 3 hours reflux, the solution was allowed to cool, more KOH was added and the refluxing continued whereupon the reaction mixture became a dark purple color. This was then allowed to cool to room temperature. This was diluted with ether and washed with saturated aqueous NaHCO$_3$ solution. The layers were separated, the water layer extracted with ether, the ether extracts were combined, and dried over MgSO$_4$. The solvents were evaporated to give a brown oil. This proved to be a mixture of 1-indanone and product. The brown oil was washed with hexane and ether in order to extract 1-indanone. In this way, 15.1 g (24%) of pure CH$_2$(1-indanone)$_2$ were isolated.

$^1$H NMR (CDCl$_3$): δ 7.75 (d, 2H), 7.6 (t, 2H), 7.45 (d, 2H), 7.4 (t, 2H), 3.4 (m, 2H), 2.95 (m, 4H), 2.05 (t, 2H). $^{13}$C NMR (CDCl$_3$): δ 208.7 (CO), 153.9 (C), 137.0 (C), 135.4 (CH), 128.0 (CH), 127.1 (CH), 124.5 (CH), 46.5 (CH$_2$), 33.6 (CH).

15.0 g (54 nunol) of CH$_2$(1-indanone)$_2$, prepared as described above, and 24.3 g (2.4 equiv.) of tosyl hydrazine were placed in a 250 ml round-bottom flask and 100 ml EtOH added. Then 10 drops of 37% HCl were added and the reaction mixture brought to reflux under nitrogen. On coming to reflux, everything dissolved and a clear brown solution resulted. After refluxing for 10 minutes, a white jelly-like material began to precipitate. This was washed with MeOH and then dried under vacuum. This gave 21 g (63%) of the bis(hydrazone). 10.8 g (17.6 mmol) of the bis (hydrazone), suspended in 250 ml N,N,N',N'-tetramethyl-ethylene diamine (TMEDA) in a large Schlenk tube, was slowly added to 15.2 g (141 mmol, 8 equivalents) of lithium diisopropylamide, dissolved in 50 ml TMEDA and cooled to 0° C. The solution changed from yellow to purple and then to dark purple. It was allowed to warm to room temperature and then decanted onto ice to give a yellow solution. On washing with 100 ml aqueous NaHCO$_3$ the solution became purple. This was extracted copiously (3×250 ml) with Et$_2$O, the Et$_2$O extracts combined and dried over MgSO$_4$. These were evaporated to a brown oil which was extracted with pentane. Working up of the pentane extracts afforded 0.59 g (14%) of bis(2-indenyl)methane.

$^1$H NMR (CDCl$_3$): δ 7.38 (d, 2H), 7.28 (t, 2H), 7.25 (d, 2H), 7.12 (t, 2H), 6.6 (s, 2H, =CH), 3.65 (s, 2H, bridge CH$_2$), 3.38 (s, 4H, 2×CH$_2$). $^{13}$C NMR(CDCl$_3$): δ 148.6 (C), 145.9 (C), 143.8 (C), 128.5 (CH), 126.8 (CH), 124.4 (CH), 124.0 (CH), 120.7 (=CH), 41.4 (CH$_2$), 33.63 (CH$_2$).

(b) Preparation of the zirconocene dichloride 0.29 g (1.19 mmol) of bis(2-indenyl)methane, prepared as described above, were dissolved in 40 ml ether and cooled to −78° C. Then 1.6 ml of a 1.6 M solution of n-BuLi in hexane (2.1 equivalents) were added by syringe. It was allowed to warm to room temperature. After 90 minutes at room temperature it was cooled to −78° C. and 0.29 g ZrCl$_4$, suspended in 30 ml Et$_2$O, was added. On allowing to warm to room temperature and stirring for 2 hours, the color changed from brown to yellowish. The solvent was removed under vacuum and the powder washed with Et$_2$O and then hexane to give 300 mg of methylene-bis(2-indenyl) zirconium dichloride as a yellow powder.

$^1$H NMR (CD$_2$Cl$_2$): δ 7.51 (dd, 4H), 7.24 (dd, 4H), 6.1 (s, 4H, =CH), 4.28 (s, 2H, bridge CH$_2$).

POLYMERIZATION TRIALS

EXAMPLES 1–13 and COMPARATIVE EXAMPLES A–E

Ethylene homopolymerization

A 200 ml glass autoclave, equipped with magnetic stirrer, temperature indicator and feeding line for the ethylene, was purified and fluxed with ethylene at 35° C. Then 90 ml of n-hexane were charged at room temperature. The catalytic system was prepared by adding to 10 ml of hexane, in the following order, first the aluminum cocatalyst indicated in Table 1, then, in the case of TIOA and TIBAL, water in an amount to give a molar ratio Al/H$_2$O=2.1 and finally, after 5 minutes stirring, the metallocene indicated in Table 1 dissolved in the lowest possible amount of toluene. After further five minutes stirring the thus obtained catalyst solution was introduced into the autoclave under an ethylene flow. Then the temperature was brought to 80° C. and kept constant for the duration of the polymerization. The autoclave was pressurized to 4.6 bar and the total pressure was kept constant by feeding ethylene. After the time indicated in Table 1 the polymerization was interrupted by cooling to room temperature, degassing the reactor and introducing 1 ml of methanol. The thus obtained polymer was washed with acidic methanol, then with methanol and dried in oven at 60° C. under vacuum.

Polymerization reactions of Examples 3–5 were carried out following the above procedure, with the difference that a 2.3 L reactor and 1L hexane were used and, during the polymerization, the autoclave was pressurized to 10 bar and the total pressure was kept constant by feeding ethylene. Finally, the polymerization of Example 5 was carried out in the presence of H$_2$ (0.2 bar).

The polymerization conditions and the characterization data of the obtained polymers are indicated in Table 1.

From the obtained results, it is evident that the bridged zirconocene compounds and the catalysts containing them according to the present invention are unexpectedly much more active than the ones known in the state of the art (in particular having bridged bis(1-indenyl) ligands), independently on the cocatalyst used. Furthermore, the gist of the present invention is the possibility of obtaining ethylene homopolymers having low Mw values (endowed with I.V.<0.7), unexpectedly much lower than the ones obtainable with the metallocene/alumoxane catalyst systems known in the art.

EXAMPLES 14–23

Ethylene/1-hexene copolymerization

The same procedure as that of Examples 1–13 and comparative A–E was followed with the exception that, instead of the hexane, 100 ml of a heptane/1-hexene solution was used (the amounts of 1-hexene are those indicated in Table 2, the rest to 100 ml being heptane) and that the temperature of polymerization was 70° C. When TIOA was used as cocatalyst, water was added in amounts to give a molar ratio Al/H$_2$O=2.1.

The polymerization conditions and the characterization data of the obtained polymers are indicated in Table 2.

The reported results demonstrate that the bridged zirconocene compounds and the catalysts containing them according to the present invention allow to obtain polymers having low Mw and narrow MWD values.

Furthermore, the obtained copolymers showed a completely homogeneous distribution of the comonomer along the polymer chain, as confirmed by the results reported in Table 3.

EXAMPLES 24–41

Propylene homopolymerization 500 molar equivalents of MAO (10% wt. toluene solution) were premixed with the amount of the metallocene indicated in Table 4 and stirred in a drybox at 20° C. for a known time, between 1.5 hours and overnight. Into a 5 L autoclave containing 1.6 Kg propylene, MAO was injected and subsequently (5 minutes later) the premix added. The total Zr:MAO ratio is indicated in Table 4. The reactor was held at 30° C. for 1 minute and then the temperature raised with a temperature gradient of 4° C./minute to 50° C. Polymerization was continued for the time indicated in Table 4 at 50° C. After the time indicated in Table 4 the polymerization was interrupted by rapidly venting the excess of propylene to the incinerator. The thus obtained polymer was isolated according to standard procedures. The polymerization conditions and the characterization data of the obtained polymers are indicated in Table 4.

EXAMPLES 42–48

Ethylene/propylene copolymerization

It was worked as in Examples 24–41, with the exception that the polymerization was conducted in a 25 L autoclave containing 7.5 kg propylene and with an ethylene/propylene feed ratio of about 6 mol % (liquid phase). This is equivalent to a 3.3 bar ethylene overpressure. The feed ratio (mol %) of ethylene in the Examples is reported in Table 5. The feed ratio was kept constant throughout the polymerization by adding ethylene on demand. The total amount of MAO added was 11.0 g. The MAO was used as a toluene solution containing 4.84% Al. The reactor temperature was 50° C. Due to effective cooling system, the copolymerizations were essentially isothermal with typical initial exotherms of 1–5° C. being observed (i.e. at maximum cooling capacity, the temperature in the autoclave rose by 1–5° C.). The copolymerization was continued for the time reported in Table 5 and then killed by injection of 2.5 mL MeOH. In several runs the copolymer adhered to the autoclave walls and so was extracted with toluene (140° C.). The toluene was removed on a rotary evaporator and the weight of this fraction added to that was directly removed from the reactor to determine the overall yield and hence activity. This fraction was not used for NMR or LVN analysis. The polymerization conditions and the characterization data of the obtained polymers are indicated in Table 5.

TABLE 1

Ethylene homopolymerization

| | Metallocene | | Cocatalyst | | Al/Zr | Time | Yield | Activity | I.V.* | | |
|---|---|---|---|---|---|---|---|---|---|---|---|
| Example | Type | mg | Type | mmol | mol/mol | (min) | (g) | (Kg/g · Zrh) | (dl/g) | Mw · 10$^{-3}$ | Mw/Mn |
| 1 | EB(2-Ind)$_2$ZrCl$_2$ | 0.100 | MAO | 0.24 | 1000 | 10 | 2.88 | 528.6 | 0.42 | | |
| 2 | " | 0.104 | TIOA | 0.25 | 1000 | 10 | 3.25 | 860.3 | 0.54 | | |
| 3 | " | 0.400 | TIOA | 0.90 | 1000 | 60 | 41 | 470 | 0.60 | | |
| 4 | " | 0.200 | TIOA | 0.10 | 2000 | 30 | 94 | 2160 | 0.56 | | 2.6 |
| 5 | " | 0.200 | TIOA | 0.10 | 2000 | 60 | 64 | 1470 | 0.47 | 23 | 2.6 |
| 6 | r-EB(1-Me-2-Ind)$_2$ZrCl$_2$ | 0.100 | MAO | 0.14 | 600 | 10 | 1.20 | 352.5 | 0.47 | | |
| 7 | " | 0.100 | TIBAL | 0.23 | 1000 | 10 | 3.66 | 1075 | 0.59 | | |

TABLE 1-continued

Ethylene homopolymerization

| Example | Metallocene Type | mg | Cocatalyst Type | mmol | Al/Zr mol/mol | Time (min) | Yield (g) | Activity (Kg/g · Zrh) | I.V.* (dl/g) | Mw · 10⁻³ | Mw/Mn |
|---|---|---|---|---|---|---|---|---|---|---|---|
| 8 | " | 0.100 | MAO | 0.23 | 1000 | 10 | 2.75 | 807.9 | 0.46 | | |
| 9 | " | 0.100 | TIOA | 0.22 | 1000 | 10 | 4.61 | 1354.3 | 0.67 | | |
| 10 | " | 0.050 | TIOA | 0.21 | 1900 | 10 | 2.30 | 1351.3 | 0.63 | 32000 | 2.3 |
| 11 | m-EB(1-Me-2-Ind)₂ZrCl₂ | 0.100 | MAO | 0.23 | 1000 | 10 | 1.92 | 564.0 | 0.36 | | |
| 12 | " | 0.100 | TIOA | 0.21 | 1000 | 10 | 1.57 | 461.2 | 0.37 | 18000 | 2.5 |
| 13 | " | 0.100 | TIBAL | 0.23 | 1000 | 10 | 1.28 | 376.0 | 0.36 | | |
| COMP. A | CH₂(2-Ind)₂ZrCl₂ | 0.300 | MAO | 0.75 | 1000 | 10 | 1.51 | 132.6 | 0.17 | | |
| COMP. B | " | 0.500 | MAO | 2.50 | 2000 | 10 | 3.39 | 178.6 | 0.12 | | |
| COMP. C | " | 0.500 | TIOA | 2.50 | 2000 | 30 | 1.54 | 27.0 | 0.20 | | |
| COMP. D | EBIZrCl₂ | 0.088 | MAO | 0.21 | 1000 | 10 | 1.31 | 409.8 | 1.38 | | |
| COMP. E | " | 0.088 | TIOA | 0.21 | 1000 | 10 | 1.18 | 369.2 | 1.60 | | |

*I.V. measured in tetrahydronaphtalene (THN) at 135° C.

TABLE 2

Ethylene/1-hexene copolymerization

| Ex. | Metallocene Type | mg | Cocatalyst TIOA mmol | Al/Zr mol/mol | C2H4 (bar) | C6 (ml) | Time (min) | Yield (g) | Activity (Kg/gZr.h) | I.V.* (dl/g) | C6 (% w) | Tm (° C.) | ΔHf (J/g) | Mw −10⁻³ | Mw/Mn |
|---|---|---|---|---|---|---|---|---|---|---|---|---|---|---|---|
| 14 | EB(2-Ind)₂ZrCl₂ | 0.077 | 0.18 | 1000 | 4.4 | 0 | 15 | 1.65 | 395.9 | 0.60 | 0 | 132.9 | 233 | — | — |
| 15 | " | 0.074 | 0.18 | 1000 | 4.5 | 5 | 15 | 1.70 | 423.9 | 0.75 | 1.5 | 127.2 | 213 | — | — |
| 16 | " | 0.083 | 0.20 | 1000 | 4.5 | 5 | 15 | 2.25 | 497.5 | 0.54 | 1.7 | 124.2 | 188 | — | — |
| 17 | " | 0.074 | 0.18 | 1000 | 4.5 | 10 | 15 | 2.62 | 653.4 | 0.60 | 2.9 | 120.9 | 162 | — | — |
| 18 | " | 0.083 | 0.20 | 1000 | 4.4 | 15 | 15 | 3.18 | 703.2 | 0.57 | 4.0 | 118.4 | 152 | — | — |
| 19 | " | 0.100 | 0.24 | 1000 | 4.2 | 50 | 30 | 3.88 | 356.1 | 0.49 | 9.9 | 116.0 | 86 | 22 | 2.6 |
| 20 | r-EB(1-Me-2-Ind)₂ZrCl₂ | 0.050 | 0.12 | 1000 | 4.4 | 15 | 20 | 3.72 | 1092.8 | 0.59 | 5.4 | 116.7 | 154 | — | — |
| 21 | " | 0.050 | 0.11 | 1000 | 4.2 | 50 | 30 | 5.60 | 1096.7 | 0.58 | 16.4 | 95.3 | 90 | 33 | 2.2 |
| 22 | m-EB(1-Me-2-Ind)₂ZrCl₂ | 0.100 | 0.23 | 1000 | 4.4 | 15 | 20 | 3.20 | 470.0 | 0.30 | 9.9 | 108.9 | 139 | 18 | 2.3 |
| 23 | " | 0.200 | 0.45 | 1000 | 4.2 | 50 | 30 | 6.46 | 316.3 | 0.33 | 31.2 | amorphous | | — | — |

*I. V. measured in tetrahydronaphtalene (THN) at 135° C.

TABLE 3

| Parameter | Unit | Example 18 | Example 19 |
|---|---|---|---|
| Traid distribution EEE | mol % | 95.73 | 89.42 |
| HEE | mol % | 2.90 | 7.05 |
| HEH | mol % | 0.00 | 0.00 |
| EHE | mol % | 1.37 | 3.53 |
| HHE | mol % | 0.00 | 0.00 |
| HHH | mol % | 0.00 | 0.00 |
| Dyad distribution EE | mol % | 97.2 | 92.9 |
| EH | mol % | 2.80 | 7.1 |
| HH | mol % | 0.00 | 0.00 |
| Calculated parameters n(E) | | 70.4 | 27.1 |
| r₁ | | 182 | 235 |
| r2 | | 0 | 0 | wherein:

$r_1 = 2[EE]/[EH] - x$
$r_2 = 2[HH] - x/[EH]$
$x = [E]/[H]$
n(E) is the average ethylene sequences length = (2EE/EH) + 1

TABLE 4

Propylene homopolymerization

| Ex. | Metallocene Type | Al/Zr μmol | H₂ mol/mol | Time (mol %) | Yield (min) | Activity (g) | I.V.* (Kg/gZr · h) | NMR Mn | 2,1(%) |
|---|---|---|---|---|---|---|---|---|---|
| 24 | EB(2-Ind)₂ZrCl₂ | 4.0 | 1000 | 0 | 61 | 0.7 | 1.9 | 0.36 | 1700 | 9.4 |
| 25 | " | 2.0 | 10000 | 2–3 | 60 | 97 | 530 | — | 500 | |

TABLE 4-continued

Propylene homopolymerization

| | Metallocene | | Al/Zr | $H_2$ | Time | Yield | Activity | I.V.* | NMR | |
|---|---|---|---|---|---|---|---|---|---|---|
| Ex. | Type | µmol | mol/mol | (mol %) | (min) | (g) | (Kg/gZr · h) | (dl/g) | Mn | 2,1(%) |
| 26 | r-EB(1-Me-2-Ind)$_2$ZrCl$_2$ | 3.75 | 5400 | 0 | 60 | 5.5 | 16 | 0.25 | 2700 | 2.7 |
| 27 | " | 4.0 | 5000 | 2–3 | 5 | 277 | 9100 | — | 1100 | |
| 28 | " | 0.5 | 40200 | 2–3 | 60 | 284 | 6240 | — | 850 | |
| 29 | m-EB(1-Me-2-Ind)$_2$ZrCl$_2$ | 4.0 | 5000 | 0 | 60 | 5.4 | 15 | — | 3600 | 0.4 |
| 30 | EB(1,3-diMe-2-Ind)$_2$ZrCl$_2$ | 4.0 | 5000 | 0 | 60 | 22 | 60 | — | 5500 | 0.2 |
| 31 | " | 0.5 | 40000 | 2.7 | 60 | 230 | 5030 | — | 1900 | 0.5 |
| 32 | 4:1 r/m-EB(4-Ph-2-Ind)$_2$ZrCl$_2$ | 4.0 | 5000 | 0 | 60 | 1.8 | 5 | — | 3000 | 9.9 |
| 33 | " | 0.5 | 40000 | 2.7 | 60 | 15.1 | 330 | — | 1300 | 0.2 |
| 34 | 7:3 r/m-EB(4-Ph-1-Me-2-Ind)$_2$ZrCl$_2$ | 4.0 | 5000 | 0 | 30 | 246 | 1350 | — | 15500 | 0.4 |
| 35 | " | 0.5 | 40000 | 2.7 | 60 | 49 | 1070 | — | 1000 | 0.1 |
| 36 | m-EB(4-Ph-1-Me-2-Ind)$_2$ZrCl$_2$ | 4.0 | 5000 | 0 | 60 | 101 | 280 | — | 15100 | <0.1 |
| 37 | " | 0.5 | 40000 | 2.7 | 60 | 41 | 900 | — | 1000 | 0.2 |
| 38 | r-EB(1-Et-2-Ind)$_2$ZrCl$_2$ | 4.0 | 5000 | 0 | 60 | 2.5 | 7 | — | — | — |
| 39 | " | 0.5 | 40000 | 2.4–3.6 | 60 | 60.2 | 1320 | — | 1000 | 0.5 |
| 40 | m-EB(1-Et-2-Ind)$_2$ZrCl$_2$ | 4 | 5000 | 0 | 60 | 4 | 11 | — | 3700 | 0.9 |
| 41 | " | 0.5 | 40000 | 2–2.5 | 60 | 231 | 5080 | — | 1800 | 0.3 |

*I.V. measured in decalin at 135° C.

TABLE 5

Ethylene/propylene copolymerization

| | Metallocene | | Al/Zr | $C_2H_4$ | $H_2$ | Time | Yield | Activity | I.V.* | C3 |
|---|---|---|---|---|---|---|---|---|---|---|
| Ex. | Type | µmol | mol/mol | (mol %) | (mol %) | (min) | (g) | (Kg/gZr · h) | (dl/g) | (mol %) |
| 42 | EB(2-Ind)$_2$ZrCl$_2$ | 4.0 | 1000 | 5.6 | 0 | 40 | 225 | 920 | 0.46 | 19.0 |
| 43 | " | 2.0 | 40000 | 5.6 | 0 | 45 | 44.5 | 1300 | 0.47 | 13.8 |
| 44 | r-EB(1-Me-2-Ind)$_2$ZrCl$_2$ | 0.47 | 42900 | 5.5 | 0 | 47 | 290 | 8660 | 0.69 | 23.4 |
| 45 | " | 0.94 | 21500 | 5.5 | 0 | 17 | 260 | 10660 | 0.71 | 17.9 |
| 46 | m-EB(1-Me-2-Ind)$_2$ZrCl$_2$ | 1.0 | 20400 | 5.5 | 0 | 33 | 250 | 4992 | 0.53 | 24.1 |
| 47 | r-EB(1-Et-2-Ind)$_2$ZrCl$_2$ | 0.5 | 40200 | 6.2 | 0 | 65 | 181 | 6400 | 0.93 | 26.9 |
| 48 | m-EB(1-Et-2-Ind)$_2$ZrCl$_2$ | 0.5 | 40200 | 6.2 | 0 | 60 | 570 | 12500 | 0.63 | 23.3 |

*I.V. measured in decalin at 135° C.

What is claimed is:

1. A catalyst for the polymerization of olefins comprising the produce obtainable by contacting:

(A) one or more bridged zirconocene compounds of formula (I):

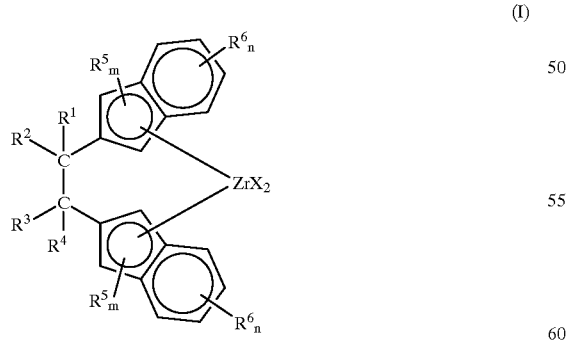

(I)

wherein $R^1$, $R^2$, $R^3$ and $R^4$, the same or different from each other, are selected from the group consisting of hydrogen, linear or branched, saturated or unsaturated, $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more Si or Ge atoms, or wherein two substituents of $R^1$, $R^2$, $R^3$ and $R^4$ form a ring having from 4 to 8 carbon atoms; $R^5$ and $R^6$, the same or different from each other, are selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl and $C_7$–$C_{20}$ arylalkyl radicals, optionally containing one or more Si or Ge atoms, or wherein two vicinal $R^6$ substituents on the same indenyl group form a ring having from 4 to 8 carbon atoms;

m is an integer ranging from 0 to 2; n is an integer ranging from 0 to 4; the groups X, the same or different from each other, are hydrogen, halogen, —R, —OR, —SR, —NR$_2$ or —PR$_2$, wherein R is selected from the group consisting of linear or branched, saturated or unsaturated, $C_1$–$C_{20}$ alkyl, $C_3$–$C_2$, cycloalkyl, $C_6$–$C_{20}$ aryl, $C_7$–$C_{20}$ alkylaryl and $C_7$–$C_{20}$ arylalkyl radicals, optionally containing one or more Si or Ge atoms; and (B) a suitable activating cocatalyst.

2. The catalyst according to claim 1, characterized in that said activating cocatalyst is a linear, branched or cyclic alumoxane, containing at least one group of the type:

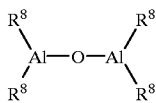

wherein the substituents $R^8$, the same or different from each other, are linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl, $C_7$–$C_{20}$ arylalkyl radicals, or groups —O—Al($R^8$)$_2$.

3. The catalyst according to claim 2, characterized in that said alumoxane is selected from the group consisting of methylalumoxane, tetra-isobutyl-alumoxane, tetra-2,4,4-trimethylpentylalumoxane, tetra-2-methyl-pentylalumoxane and mixtures thereof.

4. The catalyst according to claims 1, characterized in that said activating cocatalyst is the product of the reaction between water and an organometallic aluminum compound of formula $AlR^8{}_3$ or $Al_2R^8{}_6$, wherein the groups $R^8$, the same or different from each other, are a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups.

5. The catalyst according to claim 1, characterized in that said activating cocatalyst is a compound capable of forming an alkyl zirconocene cation, having formula $Y^+Z^-$, wherein $Y^+$ is a Bronsted acid and $Z^-$ is a compatible non coordinating anion.

* * * * *

UNITED STATES PATENT AND TRADEMARK OFFICE
CERTIFICATE OF CORRECTION

PATENT NO. : 6,306,791 B1
DATED : October 23, 2001
INVENTOR(S) : Colin Schaverien et al.

It is certified that error appears in the above-identified patent and that said Letters Patent is hereby corrected as shown below:

Column 38,
Line 60, please change "$C_2$" to -- $C_{20}$ --.

Signed and Sealed this

Ninth Day of April, 2002

Attest:

Attesting Officer

JAMES E. ROGAN
Director of the United States Patent and Trademark Office